US012622747B2

(12) United States Patent　　　(10) Patent No.:　US 12,622,747 B2

Fung et al.　　　　　　　　　　　　(45) Date of Patent:　　May 12, 2026

---

(54) DEVICES AND METHODS FOR LEFT ATRIAL APPENDAGE CLOSURE

(71) Applicant: AtriCure, Inc., Mason, OH (US)

(72) Inventors: Gregory W. Fung, Redwood Shores, CA (US); Randall J. Lee, Hillsborough, CA (US); Russell Pong, Newark, CA (US); Robert L. Clark, III, Hayward, CA (US); Arnold M. Escano, San Jose, CA (US)

(73) Assignee: AtriCure, Inc., Mason, OH (US)

( * ) Notice: Subject to any disclaimer, the term of this patent is extended or adjusted under 35 U.S.C. 154(b) by 190 days.

(21) Appl. No.: 18/514,913

(22) Filed: Nov. 20, 2023

(65) Prior Publication Data

US 2024/0081903 A1　　　Mar. 14, 2024

Related U.S. Application Data

(63) Continuation of application No. 17/062,406, filed on Oct. 2, 2020, now Pat. No. 11,844,566, which is a (Continued)

(51) Int. Cl.
　　*A61B 18/14*　　　　(2006.01)
　　*A61B 17/12*　　　　(2006.01)
　　(Continued)

(52) U.S. Cl.
　　CPC .... *A61B 18/1492* (2013.01); *A61B 17/12013* (2013.01); *A61B 2017/00243* (2013.01);
　　(Continued)

(58) Field of Classification Search
　　CPC ..................... A61B 18/1492; A61B 17/12013
　　(Continued)

(56) References Cited

U.S. PATENT DOCUMENTS

| | | |
|---|---|---|
| 11,844,566 B2 | 12/2023 | Fung et al. |
| 2002/0143326 A1 | 10/2002 | Foley et al. |

(Continued)

FOREIGN PATENT DOCUMENTS

| | | |
|---|---|---|
| CA | 2796267 | 10/2011 |
| CA | 2838539 | 12/2012 |

(Continued)

OTHER PUBLICATIONS

U.S. Appl. No. 17/062,406, filed Oct. 20, 2020.
U.S. Pat. No. 10,799,288 issued Oct. 13, 2020, Fung et al.
U.S. Pat. No. 10,258,408 issued Apr. 16, 2019, Fung et al.

*Primary Examiner* — Nicole F Johnson
(74) *Attorney, Agent, or Firm* — Levine Bagade Han LLP

(57)　　　　　ABSTRACT

Described here are devices, systems, and methods for closing the left atrial appendage. The methods described here utilize a closure device for closing the left atrial appendage and guides or expandable elements with ablation or abrading elements to ablate or abrade the left atrial appendage. In general, these methods include positioning a balloon at least partially within the atrial appendage, positioning a closure assembly of a closure device around an exterior of the atrial appendage, inflating the balloon, partially closing the closure assembly, ablating the interior tissue of the atrial appendage with the inflated balloon, removing the balloon from the atrial appendage, and closing the atrial appendage with the closure assembly.

20 Claims, 13 Drawing Sheets

Related U.S. Application Data continuation of application No. 16/289,365, filed on Feb. 28, 2019, now Pat. No. 10,799,288, which is a continuation of application No. 14/530,575, filed on Oct. 31, 2014, now Pat. No. 10,258,408.

(60) Provisional application No. 61/898,382, filed on Oct. 31, 2013.

(51) Int. Cl.
*A61B 17/00* (2006.01)
*A61B 18/00* (2006.01)

(52) U.S. Cl.
CPC ............... *A61B 2017/00477* (2013.01); *A61B 2017/00876* (2013.01); *A61B 2018/0016* (2013.01); *A61B 2018/0022* (2013.01); *A61B 2018/00357* (2013.01); *A61B 2018/00577* (2013.01); *A61B 2018/141* (2013.01); *A61B 2018/142* (2013.01)

(58) Field of Classification Search
USPC ........................................................... 606/41
See application file for complete search history.

(56) References Cited

U.S. PATENT DOCUMENTS

| | | | |
|---|---|---|---|
| 2008/0243183 A1 | 10/2008 | Miller et al. | |
| 2010/0191279 A1* | 7/2010 | Kassab | A61B 17/12031 |
| | | | 606/213 |
| 2011/0082495 A1 | 4/2011 | Ruiz | |
| 2013/0144311 A1 | 6/2013 | Fung et al. | |
| 2016/0008061 A1 | 1/2016 | Fung et al. | |

FOREIGN PATENT DOCUMENTS

| | | | |
|---|---|---|---|
| WO | WO 2011/041488 | 4/2011 | |
| WO | WO 2011/129893 | 10/2011 | |
| WO | WO-2011129894 A2 * | 10/2011 | A61B 17/122 |
| WO | WO-2011130456 A1 * | 10/2011 | A61B 17/3478 |

* cited by examiner

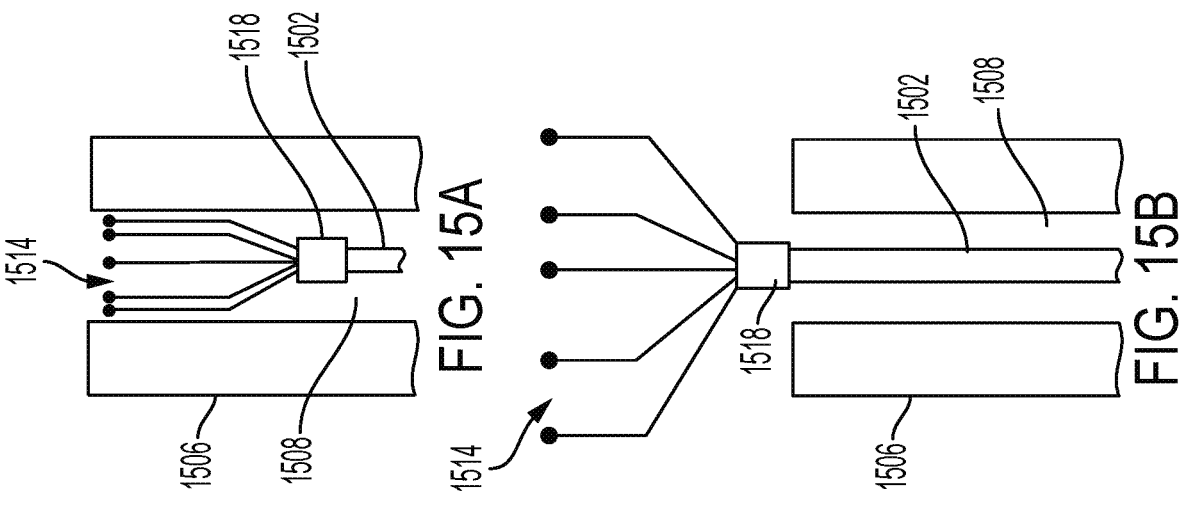
FIG. 15A
FIG. 15B
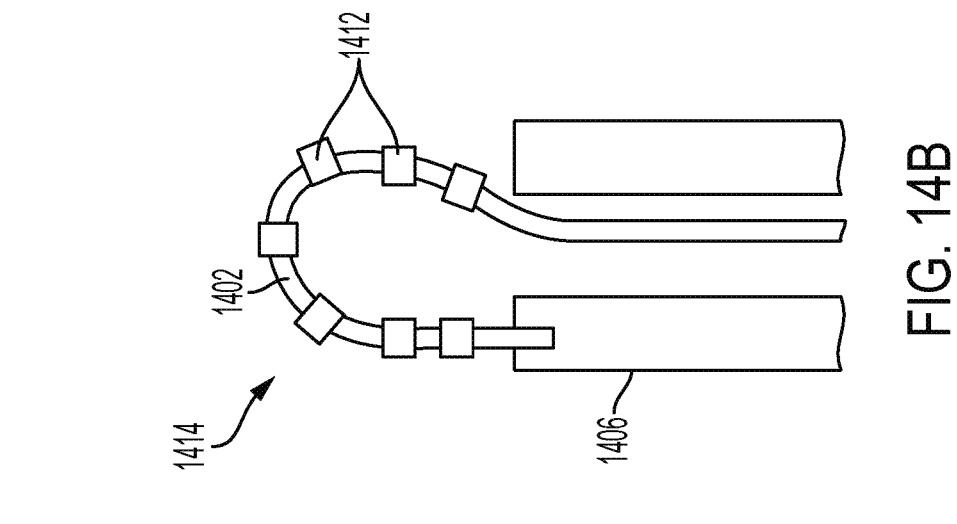
FIG. 14B
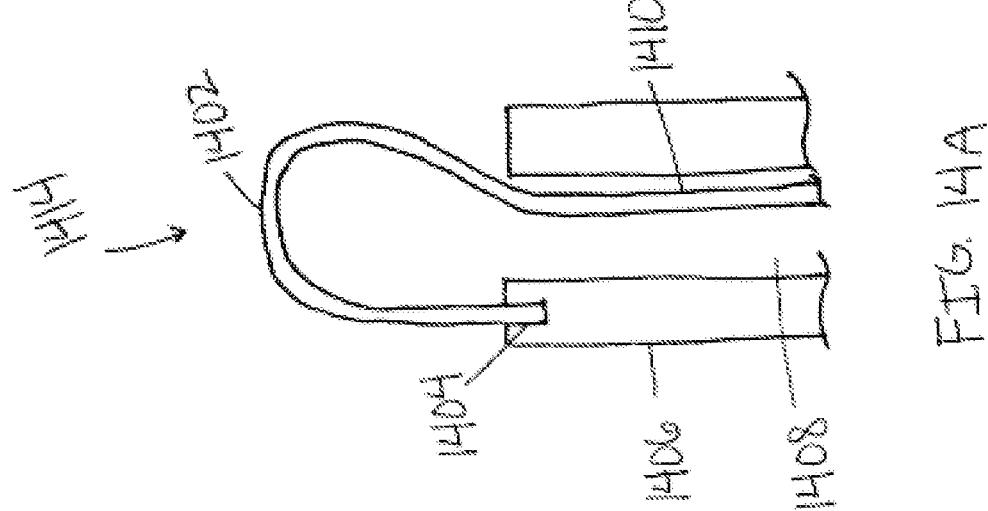
FIG. 14A

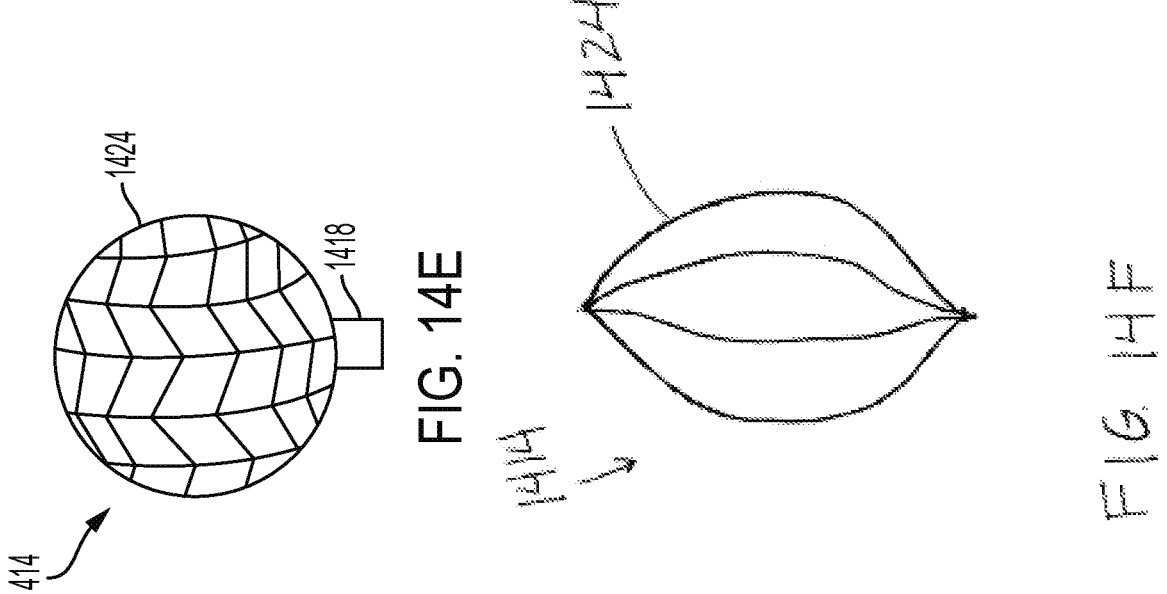
FIG. 14E
FIG. 14F
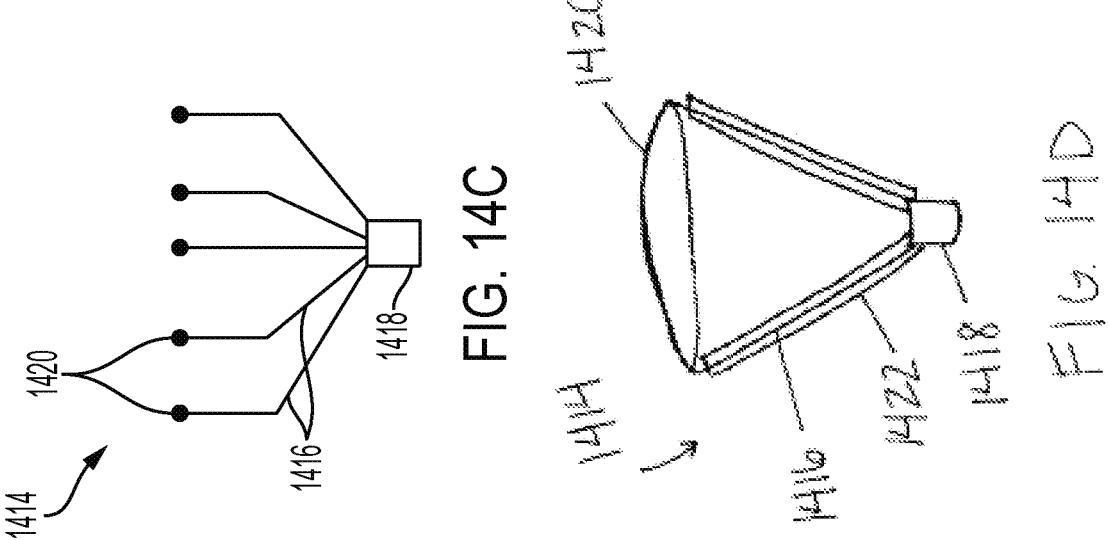
FIG. 14C
FIG. 14D

DEVICES AND METHODS FOR LEFT ATRIAL APPENDAGE CLOSURE

CROSS-REFERENCE TO RELATED APPLICATIONS

This application is a continuation application of U.S. patent application Ser. No. 17/062,406, filed on Oct. 2, 2020, which is a continuation application of U.S. patent application Ser. No. 16/289,365, filed on Feb. 28, 2019, now U.S. Pat. No. 10,799,288, issued Oct. 13, 2020, which is a continuation application of U.S. patent application Ser. No. 14/530,575, filed on Oct. 31, 2014, now U.S. Pat. No. 10,258,408, issued Apr. 16, 2019, which claims priority to U.S. Provisional patent application Ser. No. 61/898,382, filed on Oct. 31, 2013, each of which is incorporated by reference herein in its-entirety.

FIELD

This invention relates generally to systems and methods for closing tissue such as the left atrial appendage.

BACKGROUND

Atrial fibrillation is a common problem that afflicts millions of patients. Atrial fibrillation often results in the formation of a thrombus, or clot, in the appendage of the left atrium. This presents a problem, inasmuch as the thrombus can dislodge and embolize to distant organs, which may result in adverse events such as a stroke. For this reason, most patients with atrial fibrillation are treated with one or more blood thinners to help prevent the formation of a thrombus. Blood thinners, however, can present health risks of their own, especially in the elderly. These risks, such as bleeding, often require a user to make significant lifestyle changes.

Several methods have been developed to address the potential problem of thrombus formation in the left atrial appendage. One such method includes suturing the left atrial appendage along the base or ostial neck where it joins the atrial chamber. In this way, blood flow into the atrial appendage is cut off, eliminating the risk of thrombus formation therein. This is typically done through open-heart surgery, which limits the availability of the procedure to those who are at a particularly high risk, or who are otherwise undergoing an open-heart procedure. In addition, open-heart surgery requires general anesthesia and has a number of well-known risks, making it less desirable.

Other methods have also been investigated. These methods include methods of stapling the base of the appendage and methods of filling the appendage with a space occupying or occluding member. Stapling is not preferred given the fragility of the appendage and its tendency to rupture, while occlusion devices may not effectively prevent all blood flow into the appendage.

Additional devices and methods for closing the left atrial appendage or other suitable tissues would therefore be desirable. In particular, devices and methods for closing the left atrial appendage using minimally invasive, intravascular, or a combination of these techniques, would be desirable in order to avoid the need for opening the chest. Of course, additional devices for use in open surgical procedures are desirable as well, especially when those devices offer additional advantages over standard devices.

BRIEF SUMMARY

Described here are devices, systems, and methods for closing an atrial appendage such as the left atrial appendage.

In some instances, the methods described here may comprise positioning a balloon at least partially within an interior of the atrial appendage and positioning a closure assembly of a closure device around an exterior of the atrial appendage. The methods may further comprise inflating the balloon at least partially within the interior of the atrial appendage, and partially closing the closure assembly to pull interior tissue of the atrial appendage into contact with the inflated balloon. In some of these variations, the methods may further comprise ablating the interior tissue of the atrial appendage with the inflated balloon, removing the balloon from the atrial appendage, and closing the atrial appendage with the closure assembly.

In some variations, the method may further comprise positioning a distal end of a first guide element in the interior of the atrial appendage and positioning a distal end of a second guide element in a pericardial space externally of the atrial appendage. In some instances, the first guide element and the second guide element may each comprise a magnet, and the method may further comprise aligning the first guide element and the second guide element across tissue of the atrial appendage. In some variations, positioning the closure device may include advancing the closure device along the second guide element. The balloon may be part of the first guide element, or may be part of a balloon catheter. In instances where the balloon is part of the balloon catheter, positioning the balloon may comprise advancing the balloon catheter along the first guide element.

In some variations the balloon may comprise an electrode positioned on an exterior surface of the balloon, and ablating the interior tissue of the atrial appendage may comprise ablating the interior tissue of the atrial appendage with the electrode. In other variations, the balloon may comprise at least two electrodes and the method may further comprise monitoring a tissue parameter with at least one of the electrodes during ablation of the interior tissue. In yet other variations, ablating the interior tissue of the atrial appendage may comprise ablating the interior tissue of the atrial appendage using heated fluid contained in the balloon. In some variations the method may further comprise releasing a suture loop from the closure assembly to hold the atrial appendage closed. Additionally or alternatively, in some variations the closure assembly may comprise an electrode, and the method may further comprise ablating an exterior of the atrial appendage with the electrode. In some instances, the method may further comprise cryoablating an exterior surface of the atrial appendage with the closure assembly.

In other variations, the methods described here may comprise positioning a distal end of a first guide element in the interior of an atrial appendage such as the left atrial appendage, positioning a distal end of a second guide element in a pericardial space externally of the atrial appendage, and advancing a closure assembly of a closure device around an exterior of the atrial appendage along the second guide. In some of these variations, the method may further comprise withdrawing the first guide element from the interior of the atrial appendage and closing the atrial appendage with the closure assembly. The method may further comprise advancing a portion of the first guide member into contact with tissue around the ostium of the closed atrial appendage, and ablating the contacted tissue with the first guide member.

In some of these methods, the first guide element and the second guide element may each comprise a magnet, and the method may further comprise aligning the first guide element and the second guide element across tissue of the atrial appendage. In some variations, the first guide element may comprise a balloon. In some of these variations, positioning the distal end of the first guide element may comprise positioning the balloon at least partially inside the atrial appendage. In some variations, the method may further comprise advancing a balloon catheter along the first guide element to position a balloon at least partially inside the left atrial appendage. In some of these variations, the balloon may comprise an electrode positioned on an exterior surface of the balloon, and the method may further comprise ablating interior tissue of the atrial appendage using the electrodes. In some variations, the balloon may comprise at least two electrodes and the method may further comprise monitoring a tissue parameter with at least one of the electrodes during ablation of the interior tissue. In some instances, the method may further comprise cryoablating interior tissue of the atrial appendage using the balloon or ablating interior tissue of the atrial appendage using the balloon while the balloon contains heated fluid.

In some of these methods, the first guide element comprises an electrode positioned at the distal end of the first guide element. Additionally or alternatively, the method may further comprise advancing a wire from a distal end of the first guide element, wherein advancing a portion of the first guide member into contact with tissue around the ostium of the closed atrial appendage comprises advancing the wire into contact with the tissue around the ostium of the closed atrial appendage. In some of these variations, the wire may be a j-tip wire or a coiled wire. In some instances, the method may further comprise cryoablating the tissue around the ostium with the wire. In some variations, the closure assembly may comprise one or more electrodes, and the method may further comprise ablating an exterior of the atrial appendage with the one or more electrodes. In other variations, the method may further comprise cryoablating an exterior surface of the atrial appendage with the closure device.

In still other variations of the methods described here, the methods may comprise advancing a distal end of a first device in the interior of an atrial appendage such as the left atrial appendage, wherein the first device comprises a shaft, a balloon, and an electrode or abrading element positioned on the shaft proximally of the balloon, and positioning the balloon in the atrial appendage. The method may further comprise advancing a closure assembly of a closure device around an exterior of the atrial appendage, partially closing the closure assembly to place interior tissue of the atrial appendage into contact with the electrode or abrading element, and ablating or abrading the interior tissue of the atrial appendage with the electrode or abrading element. In some variations, the method may further comprise removing the first device from the atrial appendage; and closing the atrial appendage with the closure assembly. In some of these methods, the first device may comprise two or more electrodes and the method may further comprise monitoring a tissue parameter with at least one of the electrodes during ablation of the interior tissue. In some variations, the closure assembly may comprise an electrode, and the method may further comprise ablating an exterior of the atrial appendage with the electrode.

In yet other variations of the methods described here, the methods may comprise positioning a closure assembly of a closure device around an exterior of the atrial appendage, wherein the closure assembly comprises a snare, a suture loop, a retention member releasably connecting the suture loop and the snare, and an electrode on the snare between a fixed end of the snare and the retention member, closing the closure assembly to close the atrial appendage, ablating exterior tissue of the atrial appendage with the electrodes, and releasing a suture loop from the closure assembly to hold the atrial appendage closed.

Also described here are systems for closing an atrial appendage. In some variations, the systems may comprise a catheter that may be configured to be advanced endovascularly into the interior of a heart, and a closure device that may be configured to be advanced into a pericardial space. The catheter may comprise an expandable member at a distal end of the catheter and the expandable member may be configured to ablate and/or abrade tissue. In some of these systems, the expandable member may be a balloon. The closure device may comprise a lumen therethrough, a handle, and a snare loop assembly. The snare loop assembly may extend from a distal end of the elongate body and may comprise a snare, a suture loop, and a retention member that may be configured to releasably couple the snare and the suture loop. In some variations, the snare may further comprise an electrode between a fixed end of the snare and the retention member, and the electrode may be configured to ablate an exterior of the atrial appendage. In yet other variations, the snare may be configured to cryoablate an exterior of the atrial appendage.

In some variations, the system may further comprise a first guide element that may be configured to be advanced into the interior of the atrial appendage, and a second guide element that may be configured to be advanced into a pericardial space. In some instances, the second guide element may be slideably disposed within the lumen of the closure device to advance the closure device into the pericardial space. In some variations, the catheter may be part of the first guide element. In some systems, the catheter may comprise a lumen therethrough and the first guide element may be slideably disposed within the lumen of the catheter to advance the catheter into the interior of the heart.

In some systems, the expandable member may comprise at least one electrode positioned on an exterior surface of the expandable member and the expandable member may be configured to ablate interior tissue with the at least one electrode. In some instances, the expandable member may comprise a balloon and the at least one electrode may circumferentially surround the exterior surface of the balloon. In some of these systems, one electrode may circumferentially surround the exterior surface of the balloon. In other systems, the expandable member may comprise at least two electrodes and at least one electrode may be configured to monitor at least one tissue parameter during ablation of the interior tissue. In these systems, the at least one tissue parameter may comprise at least one of: temperature, ECG signals, and/or the absence of ECG signals. In some variations, the expandable member may be inflated with cryogenic fluid and may be configured to cryoablate interior tissue. In yet other variations, the catheter may further comprise a shaft on which the expandable member is mounted, the shaft may comprise at least one electrode within the expandable member, and the expandable member may be configured to ablate interior tissue with fluid heated by the at least one electrode.

In some variations of the systems described here, the system may comprise a first guide element that may be configured to be advanced into the interior of the atrial appendage, a second guide that may be configured to be advanced into a pericardial space, and a closure device that may be configured to be advanced into a pericardial space. The first guide element may comprise a shaft and an expandable member, and the shaft may comprise an ablating and/or abrading element positioned proximally of the expandable member. In some of these systems, the expandable member may be a balloon. The closure device may comprise an elongate body that may comprise a lumen therethrough, a handle, and a snare loop assembly. The snare loop assembly may extend from a distal end of the elongate body and may comprise a snare, a suture loop, and a retention member that may be configured to releasably couple the snare and the suture loop.

In some variations, the first and second guide elements may each comprise a magnet and may be configured to align across tissue of the atrial appendage. In some instances, the second guide element may be slideably disposed within the lumen of the closure device to advance the closure device into the pericardial space. Additionally or alternatively, the ablating and/or abrading element may be an electrode and the first guide may be configured to ablate interior tissue of the atrial appendage with the electrode. In some systems, the interior tissue of the atrial appendage may be tissue around an ostium of the atrial appendage. In some variations, the ablating and/or abrading element may comprise at least two electrodes and at least one electrode may be configured to monitor at least one tissue parameter during ablation of the interior tissue. In some of these variations, the at least one tissue parameter may comprise: temperature, ECG signals, and/or the absence of ECG signals. In some instances, the snare may further comprise an electrode between a fixed end of the snare and the retention member, and the electrode may be configured to ablate an exterior of the atrial appendage. In yet other instances, the snare may be configured to cryoablate an exterior surface of the atrial appendage.

In yet other variations of the systems described here, the system may comprise a first guide element that may be configured to be advanced into the interior of the atrial appendage, a second guide element that may be configured to be advanced into a pericardial space, a closure device that may be configured to be advanced into a pericardial space, and an ablating or abrading element that may be configured to ablate or abrade interior tissue of an atrial appendage. In some instances, the ablating or abrading element may comprise a j-tip, coiled, or ball-tipped wire. In some variations, the ablating or abrading element may be configured to cryoablate interior tissue of an atrial appendage.

The first guide element may comprise a proximal end, a distal end, a lumen therethrough, and a magnet on the distal end. The second guide element may comprise a proximal end, a distal end, and a magnet on the distal that may be configured to align the second guide element with the first guide element across tissue. In some variations, the first guide element may further comprise an expandable member and in some instances, the expandable member may be a balloon. The ablating or abrading element may be configured to be slideably disposed within a lumen of the first guide element and may be advanced from a distal end thereof. The second guide element may also be configured to be slideably disposed within a lumen of the closure device to advance the closure device into the pericardial space.

The closure device may comprise an elongate body that may comprise a lumen therethrough, a handle, and a snare loop assembly. The snare loop assembly may extend from a distal end of the elongate body and may comprise a snare, a suture loop, and a retention member that may be configured to releasably couple the snare and the suture loop. In some variations, the snare may further comprise an electrode between a fixed end of the snare and the retention member, and the electrode may be configured to ablate an exterior of the atrial appendage. In yet other variations, the snare may be configured to cryoablate an exterior of the atrial appendage.

BRIEF DESCRIPTION OF THE DRAWINGS

FIGS. 14A-14F depict variations of expandable members suitable for use with the systems described here.

FIGS. 15A and 15B depict cross-sectional side views of a variation of an expandable member catheter as described here.

DETAILED DESCRIPTION

Described here are systems and methods for closing the left atrial appendage. Generally, the systems and methods are configured to ablate or abrade left atrial appendage tissue before, during, or after the left atrial appendage closure procedure. In some instances, the left atrial appendage tissue may be ablated to electrically isolate the left atrial appendage from the heart. For example, for patients suffering from atrial fibrillation, electrical isolation of the left atrial appendage may limit the ability for asynchronous heart signals generated in the left atrial appendage to reach surrounding heart tissue. Additionally or alternatively, ablation or abrasion of left atrial appendage tissue may induce an inflammatory response from the left atrial appendage tissue, which may result in healing that may result in tissue fusion or otherwise help maintain closure of the left atrial appendage.

Figure 4:
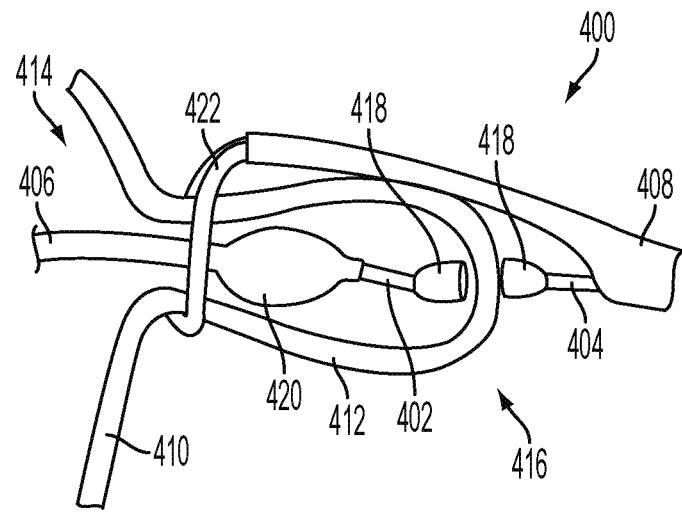
FIG. 4 depicts an illustrative variation of a system for closing the left atrial appendage.

Generally, the left atrial appendage may be closed using one or more of the systems described in U.S. patent application Ser. No. 13/490,919, filed on Jun. 7, 2012 and titled "TISSUE LIGATION DEVICES AND TENSIONING DEVICES THEREFOR," the content of which is hereby incorporated by reference in its entirety. FIG. 4 shows an illustrative variation of a closure system (400) that may be used to close the left atrial appendage. As shown there, the system may comprise a first guide element (402), a second guide element (404), an expandable member catheter (406), depicted here as a balloon catheter, and a closure device (408). Generally, the first and second guide elements may be configured to be positioned in the body and to act as guides for the advancement of devices in the body. For example, as shown in FIG. 4, a distal portion of the first guide element (402) may be introduced into the vasculature (e.g., via a femoral access site, brachial access site, or the like) and advanced into a heart (410) of a patient. In some instances, the first guide element (402) may be advanced to position a distal end of the first guide element (402) in the left atrial appendage (412). A proximal portion of the first guide element (402) may remain outside of the body such that one or more devices may be advanced along the first guide element (402) and into the body (e.g., the first guide element (402) may be slideably disposed within a lumen of a device such that the device may travel along the first guide element (402)). The device may be advanced along the first guide element (402) to position a distal portion of the device in the left atrium (414) or the left atrial appendage (412).

Similarly, a distal portion of the second guide element (404) may be positioned externally of the heart (410). For example, the second guide element (404) may be introduced into the body through an access point (e.g., intercostal access via a sternotomy, thoracotomy, or thoracotomy, right of the xiphoid process and pointed towards the patient's left shoulder, or in the costal cartilage or xiphoid process itself) and advanced to position a distal end of the second guide element into the pericardial space (416). A proximal portion of the second guide element (404) may remain outside of the body such that one or more devices may be advanced along the second guide element (404) to position a distal portion of the device in the pericardial space (416) (e.g., the second guide element (404) may be slideably disposed within a lumen of the device such that the device may travel along the second guide element (404)).

In some variations, the first guide element (402) and the second guide element (404) may be configured to align themselves across tissue of the heart. For example, in some variations, the first guide element (402) and the second guide element (404) may each comprise a magnet (418) at or near a distal end of the guide element. When the first guide element (402) and the second guide element (404) are positioned on opposite sides of heart tissue, the magnet (418) of the first guide element (402) may be attracted to the magnet (418) of the second guide element (404) (and vice versa), which may align the first and second guide elements. In some instances, as shown in FIG. 4, a distal end of the first guide element (402) may be positioned in the left atrial appendage (412), and a distal end of the second guide element (404) may be aligned with the first guide element (402) across tissue of the left atrial appendage (412) (e.g., via magnets). While shown in FIG. 4 as being aligned via magnets (418), the first guide element (402) and second guide element (404) may be manually aligned (e.g., via manipulation of the first and second guide elements under visualization such as fluoroscopy). It should also be appreciated that first and/or second guide elements may be any member suitable for advancement through the vasculature or the pericardial space, such as, for example, a catheter, wire, hollow wire, or the like.

The expandable member catheter (406) is generally configured to be advanced for endovascularly into the heart (410). For example, in some variations, the expandable member catheter (406) may be configured to be advanced along the first guide element (402) (e.g., in an over-the-wire configuration, a rapid-exchange configuration, or the like) to position a distal portion of the expandable member catheter (406) in the heart (410) (e.g., in the left atrium (414), the left atrial appendage (412) or the like). The expandable member catheter (406) may comprise an expandable member, for example, an inflatable balloon (420) or other expandable structure. The balloon (420) or expandable member may be positioned at least partially inside of the left atrial appendage (412), and may be expanded. When expanded, the balloon (420) or expandable member may press against or otherwise support a portion of the left atrial appendage (412). Additionally or alternatively, the balloon (420) or expandable member may be filled or coated with a contrast material, which may assist in visualization of the left atrial appendage (412) during the closure procedure. When the expandable member catheter (406) is positioned along a portion of the first guide element (402), the expandable member catheter (406) may be advanced over the first guide element (402) after the first guide element (402) has been positioned, or may be positioned simultaneously with the first guide element (402). In other variations, the system (400) may not comprise an expandable member catheter (406) separate from first guide element (402). In some of these variations, the first guide element (402) may comprise an inflatable balloon (420) or an expandable member, which may be expanded (e.g., in the left atrial appendage (412) as discussed above). In other variations, the system (400) may not include an expandable member positioned in the left atrial appendage (412).

The closure device (408) is generally configured to close the left atrial appendage. The closure device (408) may be advanced along the second guide element (404) to position a distal portion of the closure device (408) in the pericardial space (416). Advancement of the closure device (408) into the pericardial space (416) may also position a closure assembly (422) (such as a snare loop assembly, as will be discussed in more detail below) around an external portion of the left atrial appendage (412). The closure assembly (422) may be actuated to close the closure assembly (422) around the left atrial appendage (412), which may at least partially close the left atrial appendage (412). In some instances, the closure assembly (422) may be at least partially reopened to allow the left atrial appendage (412) to at least partially reopen and/or to remove the closure assembly (422). In some variations, the closure assembly (422) may be configured to release a suture loop or other deployable loop which may hold the left atrial appendage (412) in a closed configuration.

Figure 3:
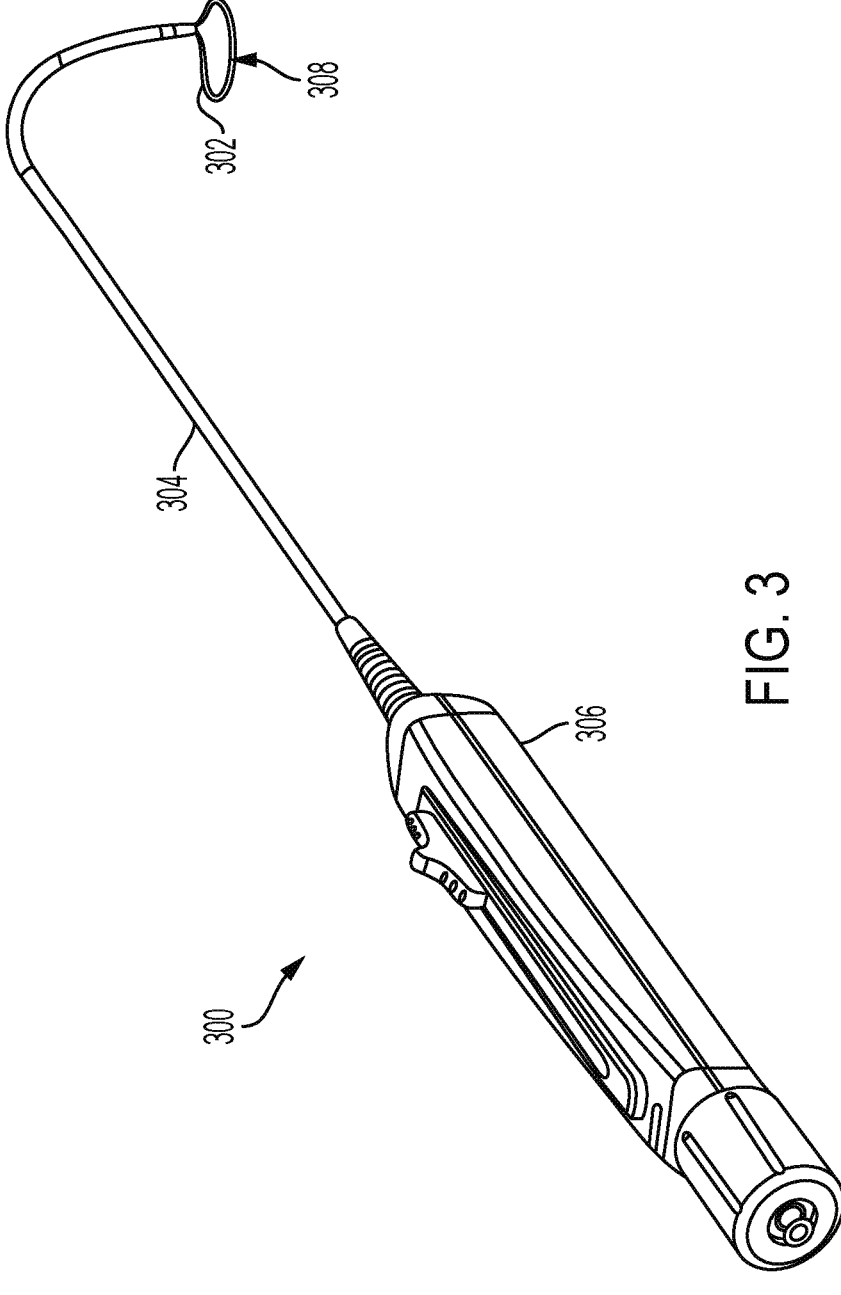
FIG. 3 is a perspective view of an illustrative closure device as described here.

FIG. 3 depicts one illustrative variation of a closure device (300) as described here. As shown there, the closure device (300) may comprise a snare loop assembly (302), an elongate body (304), and a handle (306). Generally, a portion of the snare loop assembly (302) extends from a distal portion of the elongate body (304) to form a continuous loop (308), which may allow the snare loop assembly (302) and the elongate body (304) to encircle tissue placed in the loop (308). The handle (306) may be used to control and actuate the snare loop assembly (302) through the elongate body (304) in order to increase or decrease the size of the loop (308) (e.g., increase or decrease the loop's circumference or diameter). For example, the handle (306) may advance a portion of the snare loop assembly (302) out of the elongate body (304) to increase the size of the loop (308), or may withdraw a portion of the snare loop assembly (302) into the elongate body (304) to decrease the size of the loop (308). Accordingly, the size of the loop (308) may be increased to allow the snare loop assembly (302) to be placed around tissue. Once around tissue, the size of the loop (308) may be decreased to ligate/close tissue (e.g., such as the left atrial appendage, as discussed above with respect to FIG. 4). The size of the loop (308) may then be increased to allow the tissue to be at least partially unclosed and/or to disengage the snare loop assembly (302) from tissue.

Figure 1:
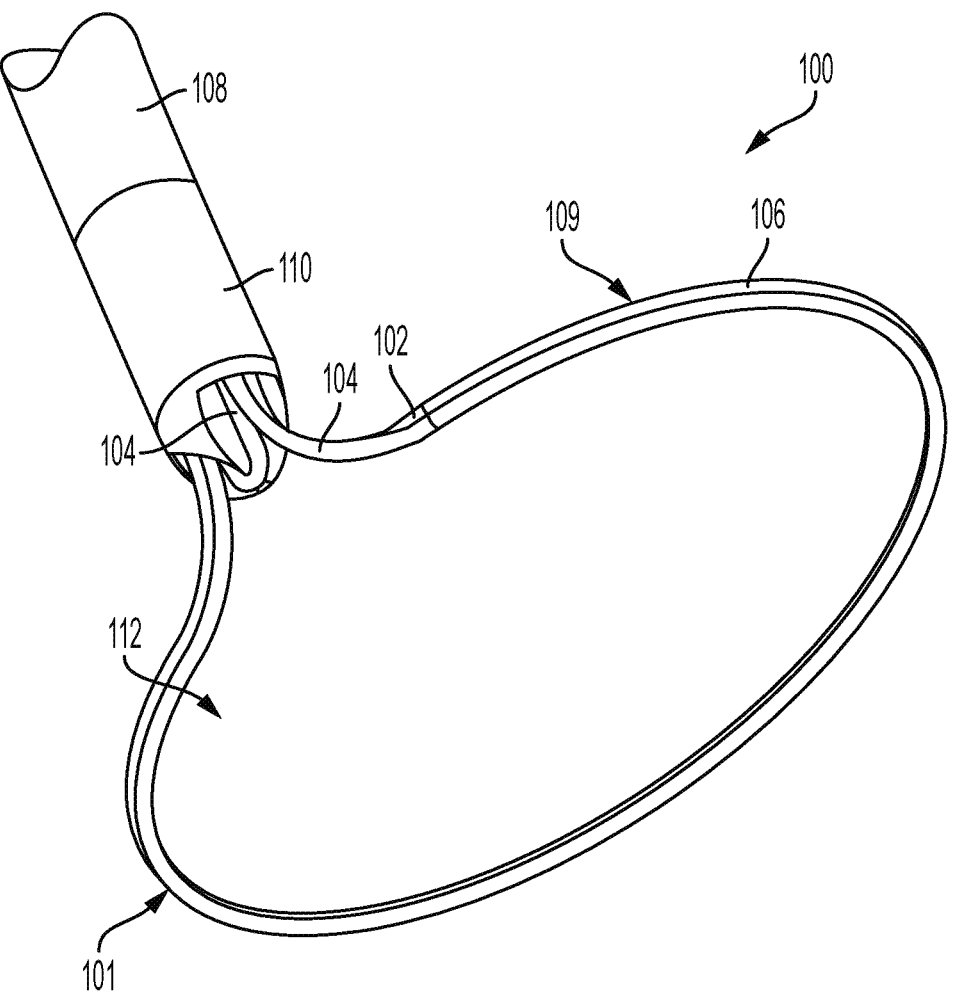
FIG. 1 depicts a distal end of an illustrative variation of a closure device having a snare loop assembly.

The snare loop assemblies of the closure devices described here generally comprise a snare and a suture loop releasably coupled thereto. For example, FIG. 1 shows a distal portion of an illustrative variation of a closure device (100) comprising a snare loop assembly (101) and an elongate body (108) having a tip (110). As shown there, the snare loop assembly (101) may comprise a snare (102), a suture loop (104), and a retention member (106), and may be disposed relative to the elongate body (108) such that at least a portion of the snare loop assembly (101) extends from the elongate body (108) (e.g., out of tip (110)). The snare loop assembly (101) is shown in FIG. 1 in an open configuration, and the portion of snare loop assembly (101) extending out of elongate body (104) may form a loop (109) having an aperture (112) therethrough, such as discussed above. The loop (109) and corresponding aperture (112) may be defined by one or more components of the snare loop assembly (101) (e.g., the snare), and may be suitable for encircling tissue such as the left atrial appendage.

Figure 2:
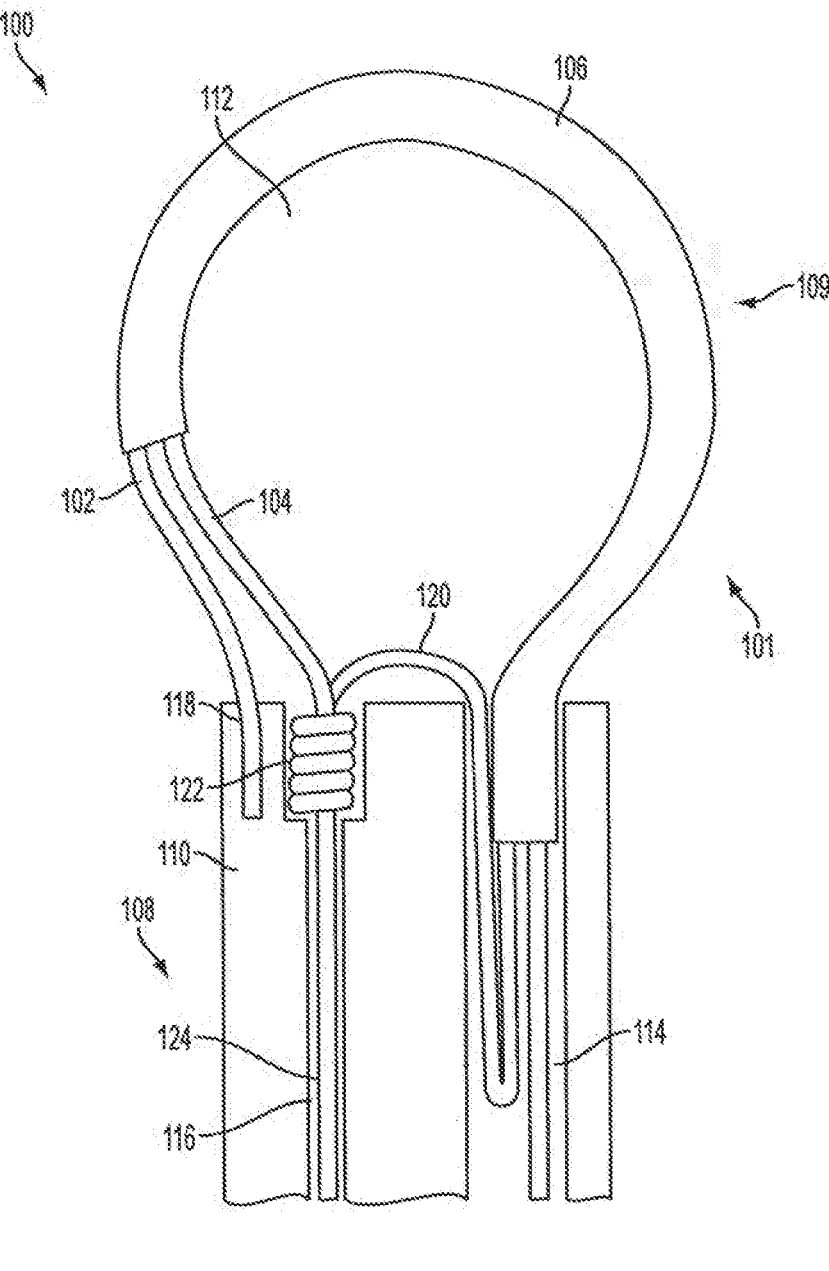
FIG. 2 shows a cross-sectional side view of the closure device of FIG. 1.

Generally, the snare (102) may be actuated (e.g., by a portion of a handle or other control portion of the closure device) to control the size of the loop (109) of the snare loop assembly (101). For example, FIG. 2 shows a cross-sectional side view of the closure device (100). As shown there, the elongate body (108) may comprise a first lumen (114) and a second lumen (116). One end (118) of the snare (102) may be fixedly attached to the elongate body (108) (e.g., attached to the tip (110)), while a second end (not shown) of the snare may pass through the first lumen (114), where it may be operatively attached to a snare control (not shown). The snare control may be configured to advance or retract the snare (102) relative to the elongate body (108), which may control the amount of the snare (102) (and with it, the snare loop assembly (101)) extending from the elongate body (108). This in turn may control the size (e.g., circumference or diameter) of the loop (109) of the snare loop assembly (101).

As mentioned above, a suture loop (104) may be releasably connected to the snare (102). For example, as shown in FIGS. 1 and 2, the suture loop (104) may be releasably coupled to the snare (102) via a retention member (106). The retention member (106) may be any suitable structure, such as a dual-lumen tube or one or more of the retention members described in U.S. patent application Ser. No. 13/490,919, which was previously incorporated by reference in its entirety. The suture loop (104) may be initially configured to have a diameter larger than that of the snare loop assembly (101) when the snare loop assembly (101) is opened (excess suture of the suture loop (104) may be housed in the elongate body (108), such as described in U.S. patent application Ser. No. 13/490,919, which was previously incorporated by reference in its entirety).

The suture loop (104) may be tightened to reduce the diameter of the suture loop (104). When the diameter of the suture loop (104) is reduced past the diameter of the loop (109) of the snare loop assembly (101), the suture loop (104) may disengage and be released from the snare loop assembly (101). For example, tightening the suture loop (104) may cause the suture loop (104) to pull or tear through one or more walls, slits, prongs, arms or the like of the retention member (106) to break the connection between the suture loop (104) and the retention member (106).

Generally, the suture loop (104) may comprise a loop portion (120), a suture knot (122) and a tail (124). As shown in FIG. 2, the suture knot (122) may be temporarily held at least partially within the tip (110) of the elongate body (108). The suture of the loop portion (120) may be pulled through the suture knot (122) to reduce the diameter of the loop portion (120). The suture tail may extend through the elongate body (108) (e.g., through the second lumen (116) of the elongate body (108)), and may be operatively attached to a suture control (not shown). The suture control may be used to pull the suture tail (124), which in turn may reduce the diameter of the loop portion (120) of the suture loop. When the snare (102) is advanced or withdrawn relative to the first lumen (114) of the elongate body (108), a portion of the suture loop (104) and the retention member (106) may also be advanced out of or withdrawn into the first lumen (114) of the elongate body (108). The suture knot (120) is preferably a one-way knot (e.g., a slip-knot), which allows the suture loop to maintain its diameter as the suture loop (104) is tightened. Additionally or alternatively, the suture loop (104) may comprise one or more unidirectional locking structures (such as those described in U.S. patent application Ser. No. 13/490,919, which was previously incorporated by reference in its entirety) which may help prevent the loop portion (120) from increasing in diameter (e.g., in response to expansive forces provided by the ligated tissue) of the suture loop (104) after it is tightened.

To close a tissue (such as the left atrial appendage) with the closure device (100), the closure device (100) may be advanced to the target tissue. Generally, the closure devices described here may be suitable for use using minimally invasive access to the left atrial appendage (e.g., through a small incision above, beneath or through the rib cage, through an incision in the costal cartilage or the xiphoid, through a port, through the vasculature, etc.), as discussed above. The moveable end of the snare (102) may be advanced relative to the elongate body (108) to increase the diameter of the loop (109) of the snare loop assembly (101) to "open" the snare loop assembly. With the snare loop assembly in an open configuration, the loop (109) may be placed around the target tissue to encircle the tissue. The moveable end of the snare (102) may be withdrawn relative to the elongate body (108) to decrease the diameter of the loop (109), which may close the snare loop assembly (101) around the tissue. With the tissue held in a closed configuration by the snare (102) and the snare loop assembly (101), the suture loop (104) may be tightened (i.e., the diameter of the loop portion (120) may be reduced by pulling the tail (124) relative to the suture knot (122)) to release the suture loop (104) from the snare loop assembly (101). Once released, the suture loop (104) may hold the tissue in a ligated configuration, and the remaining portions of the closure device (100) may be removed. In some instances, the suture loop (104) may be further tightened to reduce the diameter of the suture loop (104), as will be discussed in more detail below.

As mentioned above, one or more portions of the closure systems described here may be configured to ablate or abrade left atrial appendage tissue during the closure procedures described generally above. Generally, left atrial appendage tissue may be ablated or abraded from an endocardial approach (i.e., from an interior of the heart), an epicardial approach (i.e., from an exterior of the heart), or a combination of endocardial and epicardial approaches. For the purposes of this application, "interior tissue" of the left atrial appendage or heart will refer to internal tissue surfaces of the left atrial appendage or heart, respectively, which are accessible from the interior of the heart and/or left atrial appendage. Conversely, "exterior tissue" of the left atrial appendage or heart will refer to external tissue surfaces of the left atrial appendage or heart, respectively, which are accessible from an exterior of the heart and/or left atrial appendage.

Figure 5A:
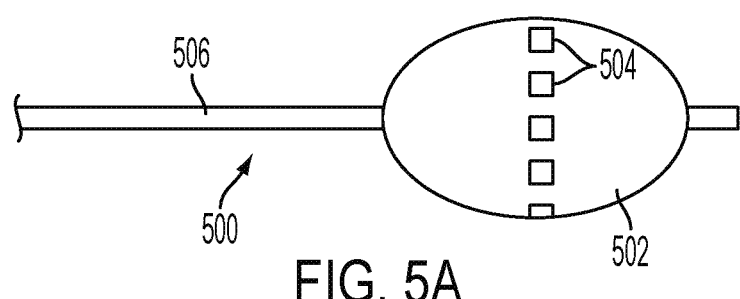
FIGS. 5A-5C depict side views of different variations of expandable member catheters suitable for use with the systems described here.
Figure 5B:
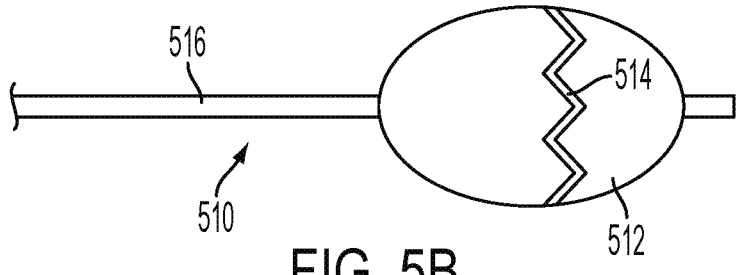
Figure 5C:
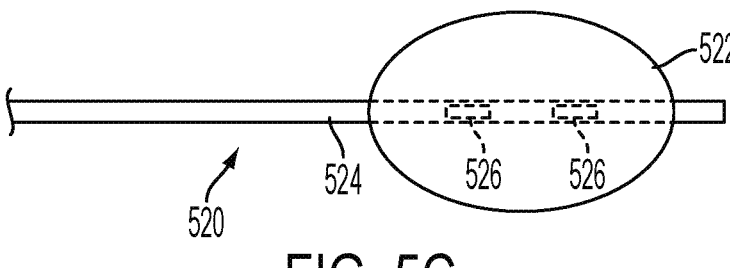

When the closure systems described here comprise an inflatable balloon or other expandable member (e.g., as part of an expandable member catheter or a first guide element), the expandable member may be configured to ablate or abrade tissue. FIGS. 5A-5C depict different variations of expandable member catheters in the form of balloon catheters configured to provide ablation energy to tissue. It should be appreciated that each of these variations may be incorporated into a guide element having an inflatable or expandable member. FIG. 5A shows a side view of a first variation of a balloon catheter (500) having an inflatable balloon (502) (although it should be appreciated that the balloon catheter (500) may comprise any suitable inflatable or expandable member). As shown there, the balloon (502) may comprise a plurality of abrading (e.g., a roughened surface, one or more barbs, spikes, hooks, or the like) or ablating (e.g., electrodes) elements (504) positioned around an exterior surface of the balloon (502). In variations used for ablation, the expansion of the balloon (502) may press one or more of the electrodes (504) against tissue, and energy may be delivered to tissue via one or more of the electrodes (504) to ablate tissue. The energy may be delivered from any suitable energy source, including but not limited to, a transducer to deliver high-intensity focused ultrasound to the tissue to locally heat and ablate it, a laser, an RF generator, etc. In some variations, one or more of the electrodes (504) may be configured to monitor one or more tissue parameters (e.g., temperature, ECG signals, the presence or absence of ECG signals) during ablation. The electrodes (504) may be electrically connected to a proximal portion of the balloon catheter (500) via one or more leads (not shown) incorporated into or on a shaft (506) of the balloon catheter (500).

In some variations, one or more of the electrodes of a balloon may be configured to circumferentially surround the balloon. For example, FIG. 5B shows another variation of a balloon catheter (510) having a balloon (512) or other expandable member. As shown there, the balloon catheter (510) may comprise at least one electrode (514) connected to the balloon (512). As shown there, the electrode (514) may be configured to circumferentially surround the balloon (512). In these variations, the electrode (514) may be flexible or otherwise configured to match the shape of the balloon (512) during inflation and deflation of the balloon (512). When the balloon (512) is expanded, the balloon (512) may press the electrode (514) into contact with tissue, and energy may be supplied to the tissue via the electrode (514) to ablate tissue. The circumferential nature of the electrode (514) may allow the electrode (514) to ablate a ring of tissue (e.g., when positioned inside of the left atrial appendage). While shown in FIG. 5B as having a single electrode (514), it should be appreciated that the balloon catheter (510) may comprise a plurality of electrodes attached to the balloon (512), such as described above. The electrodes (514) may be electrically connected to a proximal portion of the balloon catheter (510) via one or more leads (not shown) incorporate into or on a shaft (516) of the balloon catheter (510).

In other variations, the balloon catheter may be configured to thermally ablate tissue. For example, FIG. 5C shows another variation of a balloon catheter (520) having a balloon (522). As shown there, the balloon (522) may be mounted to a shaft (524), and the balloon catheter (520) may include one or more electrodes (526) mounted on the shaft (524) within the balloon (522). In these variations, fluid (e.g., saline, a saline/contrast fluid mixture) may be introduced into the balloon (522) (e.g., through an inflation port (not shown) on the shaft inside the balloon (522)) to inflate the balloon (522). RF energy may be supplied to the one or more electrodes (526), which may heat the one or more electrodes (526) and the fluid in the balloon (522). In some variations, the shaft inside of the balloon (522) may comprise one or more resistive heating elements connected to an electrical source, which may heat the fluid inside of the balloon. As the fluid in the balloon is heated, tissue in contact with the balloon may be heated to ablate the tissue. In other variations, the balloon catheter may be configured to introduce a cooled fluid into the balloon (522), which may cryoablate tissue in contact with the balloon (522). In yet other variations, the balloon catheter may be configured to introduce or apply therapeutic compounds (e.g., to promote healing) to the tissue. For example, in some instances the balloon (522) may comprise one or more porous materials such that the balloon catheter may also be used for drug delivery.

In some variations, the expandable member may comprise a loop or a metal form similar to a stent or an interior vena cava filter. For example, FIGS. 14A-14F depict embodiments of expandable members for ablating or abrading the interior tissue of the LAA. FIGS. 14A and 14B illustrate an expandable member catheter comprising an expandable member (1414) in the form of an actuatable electrode or abrading loop (1402) that may be advanced from a distal end of an elongate body (1406). The loop (1402) may be actuated (e.g., by an actuator (not pictured) on a handle or other control portion of the catheter) to control the size of loop (1402) (e.g., diameter and/or circumference) and the location of ablation or abrading. As can be seen in FIGS. 14A and 14B, the elongate body (1406) may comprise a lumen (1408) through which the distal end (1410) of the loop (1402) travels to connect to the actuator. The proximal end (1404) of the loop (1402) may be fixed to the elongate body (1406). The actuator may be configured to advance or retract the distal end (1410) of the loop (1402) relative to the elongate body (1406) to control the amount of the loop (1402) extending from the elongate body (1406) and thus the size (e.g., circumference and/or diameter) of the loop (1402).

The loop (1402) may comprise a conductive material such that the loop (1402) functions as an electrode to ablate tissue when connected to an energy source and energized. The loop (1402) may comprise a protective coating or sleeve which may help prevent inadvertent ablation when the loop (1402) is energized but not yet properly placed. In some embodiments, the loop (1402) may comprise ablating or abrading elements (1412), as depicted in FIG. 14B. In some variations, the ablating or abrading elements (1412) may comprise electrodes (e.g., RF electrodes). Additionally or alternatively, the ablating or abrading elements (1412) may comprise a roughened surface, one or more barbs, spikes, hooks, or the like. In variations in which the loop (1402) itself may be energized, the loop (1402) may also comprise abrading elements (1412). In other variations, the loop (1402) may comprise a lumen therethrough and may be connected at its distal end to a fluid source. The cryogenic fluid may flow through the loop's (1402) lumen such that the loop (1402) may be used to cryoablate the interior tissue of the LAA. In some embodiments, the loop may further comprise apertures such that the loop (1402) may deliver or dispense a therapeutic compound or an adhesive to the internal surface of the LAA, which may assist with tissue healing and/or LAA closure.

FIGS. 14D-14F depict additional embodiments of expandable members (1414) that may be utilized with the expandable member catheter. FIG. 14C depicts an expandable member comprising a plurality of arms (1416) extending distally from a central hub (1418). In some embodiments, the arms (1416) may extend outward such that their distal tips form a circle, oval, hexagon, octagon, or any other desired shape. As depicted there, each arm (1416) comprises an ablating or abrading element (1420) at its distal tip, but the arms may comprise ablating or abrading elements (1420) at any location along their lengths. Moreover, every arm (1416) need not comprise an ablating or abrading element (1420), and any number of ablating or abrading elements may be utilized. In some variations, the arms (1420) may be made of a conductive material and connected to an energy source such that the arms themselves may ablate tissue. In other variations, the expandable member (1414) may be made of a rigid polymer and may comprise abrading or ablating elements strategically placed on the expandable member (1414) based on the user's desired ablation locations. FIG. 14D depicts another variation of an expandable member (1414) comprising two arms (1416) supporting a circular ablating or abrading element (1420). The arms (1416) comprise protective coverings (1422) (e.g., a sleeve, polymer coating, etc.) which may protect the tissue when the arms (1416) also comprise abrading or ablating elements, or may otherwise damage tissue undesirably. FIGS. 14E and 14F depict variations of the expandable members (1414) comprising wire form or stent-like configurations and which comprise rounded bodies (1424) (e.g., comprising circular, oval, etc. cross-sections) in their expanded configurations. These expandable members (1414) may comprise any number of abrading or ablating elements, and/or may themselves be ablating or abrading elements (e.g., the wires that form the bodies (1424) may ablate or abrade tissue).

The expandable members may comprise a first retracted position and a second expanded position and may be constructed of a resilient material (e.g., a shape-memory material like nitinol) such that the expandable members may be advanced to the LAA in the retracted position (for example, as shown in FIG. 15A) and may be subsequently advanced into the expanded position (e.g., as shown in FIG. 15B) once proper placement is achieved. In the variation shown in FIGS. 15A and 15B, the expandable member (1514) is slideably disposed within the lumen (1508) of the catheter's elongate body (1506). The hub (1518) is connected to a second elongate body (1502) such that a user may advance the expandable member (1514) distally relative to the catheter's elongate body (1506) to move the expandable member from its retracted position (in which it is constrained) to its expanded position (in which it is no longer constrained). In some variations, the expandable member (1514) may comprise a hub (1518) at the proximal and distal ends of its arms or body. In these embodiments, the expandable member catheter may be configured such that the hub at the distal end of the expandable member catheter may be fixed and the hub at the proximal end may slide distally such that the hubs at the proximal and distal ends of the expandable member move toward each other to move the expandable element from its retracted position to its expanded position. In some variations, the expandable member (1514) may be coupled to the expandable member catheter but not disposed within its lumen.

In some embodiments, the systems described here may comprise two expandable member catheters. For example, the system may comprise a first expandable member catheter comprising a balloon (i.e., a balloon catheter) and a second expandable member catheter comprising any of the expandable members (1414) previously described (e.g., those depicted in FIGS. 14A-14F.) In these systems, a user may advance the balloon catheter into the LAA for use with the closure device, as described in detail below, and may remove the balloon catheter once the snare loop assembly has been deployed. The second expandable member catheter may then be advanced to the interior of the LAA specifically for the purpose of abrading or ablating tissue.

Figure 6A:
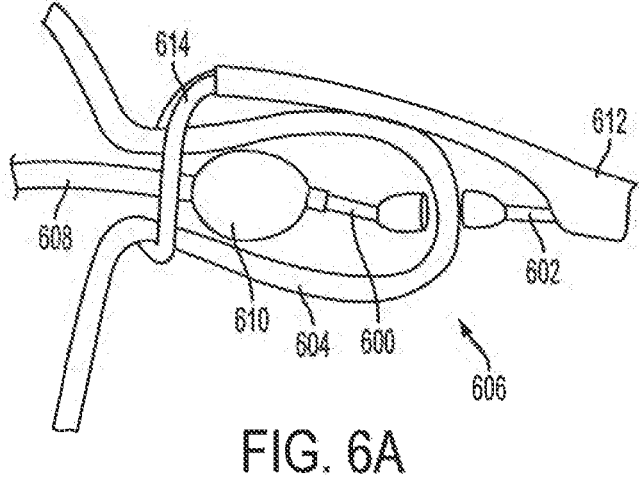
FIGS. 6A-6C depict an illustrative method of closing the left atrial appendage as discussed here.
Figure 6B:
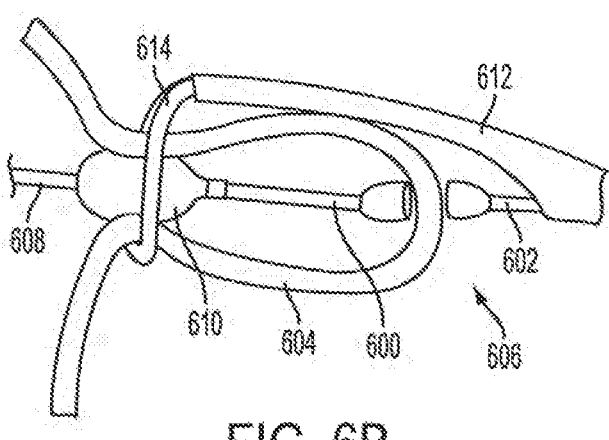
Figure 6C:
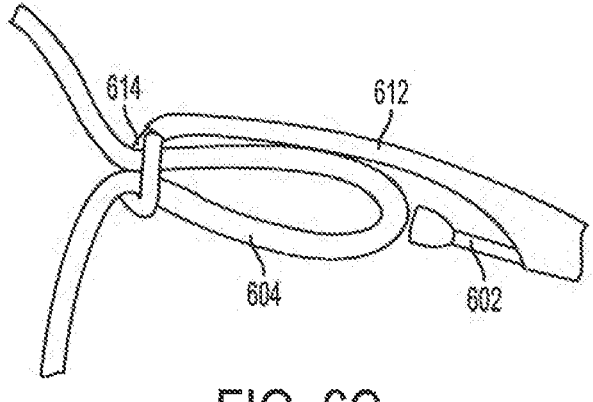

Any of the balloons described above may be used to ablate an interior tissue of the left atrial appendage. FIGS. 6A-6C depict an illustrative method by which a balloon may be used to ablate interior tissue of the left atrial appendage. As shown in FIG. 6A, a first guide element (600) and a second guide element (602) may be advanced and positioned such that a distal end of the first guide element (600) is positioned in the left atrial appendage (604) and a distal end of the second guide element (602) is positioned outside the left atrial appendage (604) in the pericardial space (606). The first guide element (600) and second guide element (602) may be aligned (e.g., using one or more magnets (not shown), such as described in more detail above with respect to FIG. 4). In some variations, a balloon catheter (608) may be advanced to position a balloon (610) in the left atrial appendage (604). In some of these variations, the balloon catheter (608) may be advanced along the first guide (600) after the first guide element (600) has been positioned in the left atrial appendage (604). In other variations, the balloon catheter (608) may be advanced simultaneously with the first guide element (600). In still other variations, the system may not comprise a balloon catheter (608), but instead the balloon (610) may be part of the first guide element (600), such that advancement of the first guide element (600) into the left atrial appendage (604) positions the balloon (610) in the left atrial appendage (604). The balloon (610) may then be inflated inside of the left atrial appendage (604).

Additionally, a closure device (612) may be advanced along the second guide element (602) to position a closure assembly (614) (such as a snare loop assemblies as discussed above with respect to FIGS. 1-3) around the left atrial appendage. With the balloon (610) positioned in the left atrial appendage (604) and the closure assembly (614) positioned around the left atrial appendage (604), the closure assembly (614) may be at least partially closed to close the left atrial appendage (604) around the balloon (610). In some variations, prior to closing the closure assembly (614), the balloon (610) and the closure assembly (614) may be positioned such that the balloon (610) is positioned inside of the closure assembly (614).

In other variations, the balloon (610) and closure assembly (614) may be initially positioned such that the closure assembly (614) is advanced past the balloon (610) and is positioned around a portion of the balloon catheter (608) (or the first guide element (600) in variations where the balloon (610) is part of the first guide element (600)) proximal of the balloon (610), such as shown in FIG. 6A. In these variations, the closure assembly (614) may be partially closed around the left atrial appendage (604) with the balloon (610) inflated to partially grab the left atrial appendage (604). With the closure assembly (614) engaging the left atrial appendage, the balloon (610) may be deflated and retracted (by retracting the balloon catheter (608), or the first guide element (600) in variations where the balloon (610) is part of the first guide element (600)) to position the balloon (610) inside of the closure assembly (614). The balloon (610) may be re-inflated to press the balloon (610) in contact with the interior tissue of the left atrial appendage (604), such as shown in FIG. 6B. In some of these variations, the closure assembly (614) may also be further closed to further pull tissue of the left atrial appendage (604).

With the left atrial appendage (604) closed around the balloon (610), the balloon (610) may be used to ablate or abrade the interior tissue that is captured by the closure assembly (614). This ablation or abrading may be done in any suitable manner. In variations where the balloon (610) comprises one or more electrodes (such as the electrodes (504) of the balloon (502) described above with respect to FIG. 5A or the electrode (514) of the balloon (512) described above with respect to FIG. 5B), the left atrial appendage (604) may be closed around the balloon (610) to press the interior tissue of the left atrial appendage in contact with some or all of the electrodes. RF energy may be supplied to the electrodes (514) to ablate the interior tissue. In variations where the balloon (610) includes one or more electrodes positioned within the balloon (such as the balloon (522) described above with respect to FIG. 5C), the electrodes may be used to heat a fluid in the balloon (610) such that the heat is transferred from the balloon to the interior tissue of the left atrial appendage (604) that is in contact with the balloon (610) to ablate tissue. In variations in which a cooled fluid is introduced into the balloon, the balloon may be used to cryoablate the interior tissue of the left atrial appendage (604) that is in contact with the balloon (610). In variations in which the balloon comprises abrading elements, the abrading elements may be used to physically damage or abrade tissue when moved against the tissue. In variations in which the balloon comprises porous materials, the balloon may be used to locally deliver therapeutic compounds to the surrounding tissue.

Following tissue ablation, the balloon (610) may be deflated and removed from the left atrial appendage (e.g., the first guide element (600) may be removed from the left atrial appendage, as well as the balloon catheter (608) in variations where the balloon (610) is part of the balloon catheter (608)). The closure assembly (614) may then be further closed to fully close the left atrial appendage (604), such as shown in FIG. 6C. In some variations, a suture loop or similar device may be deployed from the closure assembly (614) to maintain the left atrial appendage (604) in a closed configuration.

Figure 7A:
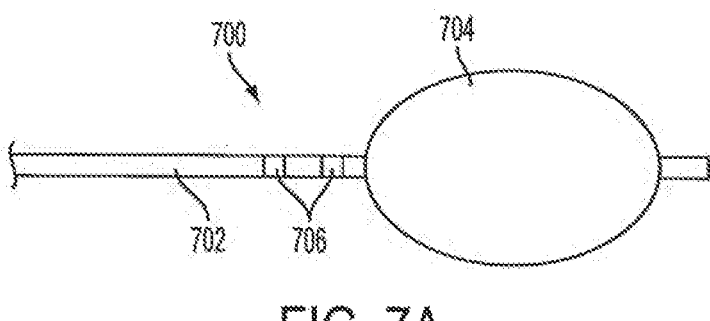
FIGS. 7A-7D depict side views of illustrative variations of devices suitable for use with the systems described here.

In other variations, one or more portions of the shaft of a balloon catheter or guide element may be used to ablate or abrade tissue. FIG. 7A shows one such variation of a balloon catheter (700) as described here. As shown there, the balloon catheter (700) may comprise a shaft (702), a balloon (704), and one or more electrodes or abrading elements (706) positioned on the shaft (702) proximally of the balloon (704). While shown in FIG. 7A as having a plurality of electrodes or abrading elements (706), in some variations the balloon catheter (700) may only comprise a single electrode or abrading element (706). In some variations, a balloon catheter may comprise at least one electrode and at least one abrading element positioned on a shaft of the balloon catheter proximal to the balloon. In some variations, elements (706) may comprise magnets, electromagnets, or magnetic material which may help with proper placement of the closure device, and more specifically, the snare loop assembly of the closure device, in embodiments in which the closure device comprises magnetic material. Elements (706) may be any combination of ablating, abrading, and magnetic elements. As discussed above, the ablating or abrading elements need not necessarily be incorporated on the balloon catheter and could instead be on a separate device that is advanced into the LAA after the balloon catheter is removed, but before the suture loop is deployed.

Figure 7B:
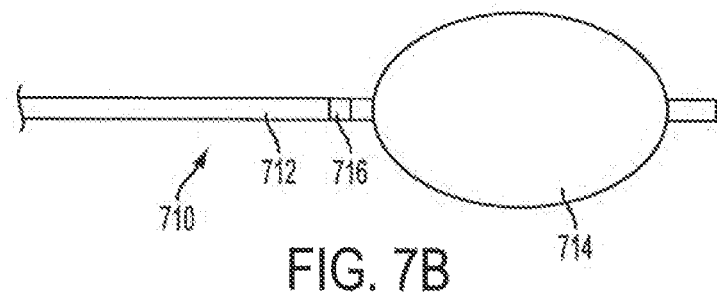

As mentioned above, the balloon catheter may comprise one or more abrading elements positioned on the shaft of the balloon catheter. For example, FIG. 7B shows one such variation of a balloon catheter (710), where the balloon catheter (710) may comprise a shaft (712), a balloon (714), and an abrading element (716) positioned on the shaft (712) proximal to the balloon (714). The abrading element (716) is generally configured such that it may physically damage or abrade tissue when moved against the tissue, as will be discussed in more detail below. For example, the abrading element (716) may include a roughened surface, one or more barbs, spikes, hooks, or the like.

Figure 7C:
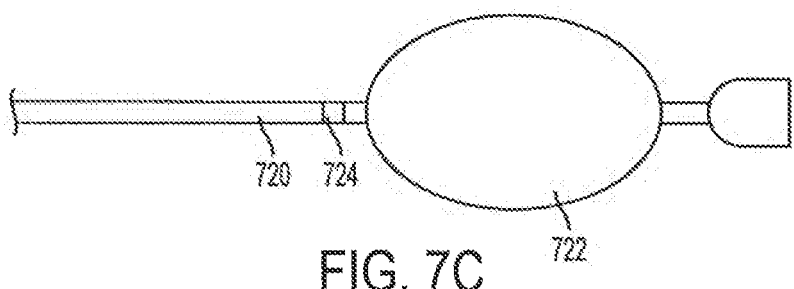
Figure 7D:
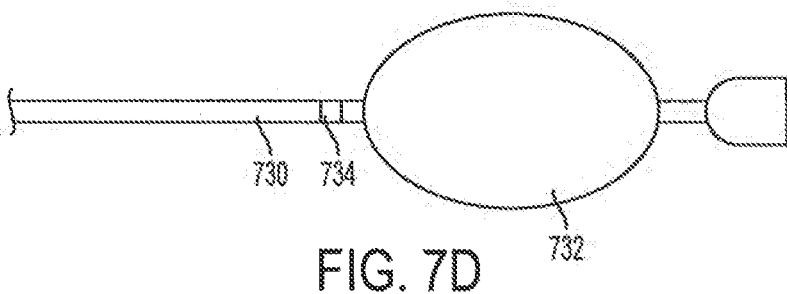

In variations where a guide element comprises a balloon (e.g., in place of having a separate balloon catheter), the guide element may comprise one or more electrodes and/or abrading elements positioned on the guide element proximally of the balloon. For example, FIG. 7C shows a variation of guide element (720) having a balloon (722) and one or more electrodes (724) positioned on the guide element (720) proximally of the balloon (722). FIG. 7D shows another variation of a guide element (730) having a balloon (732) and one or more abrading elements (734) positioned on the guide element (730) proximally of the balloon (732). In these variations, the guide element may comprise any number and combination of electrodes and or ablation elements, such as described above.

Figure 8A:
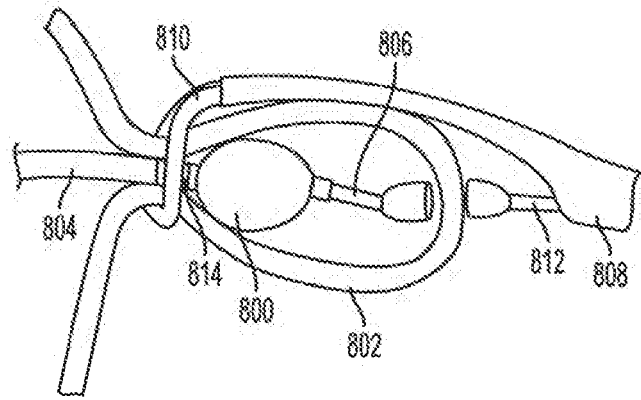
FIGS. 8A and 8B depict an illustrative method of closing the left atrial appendage as described here.
Figure 8B:
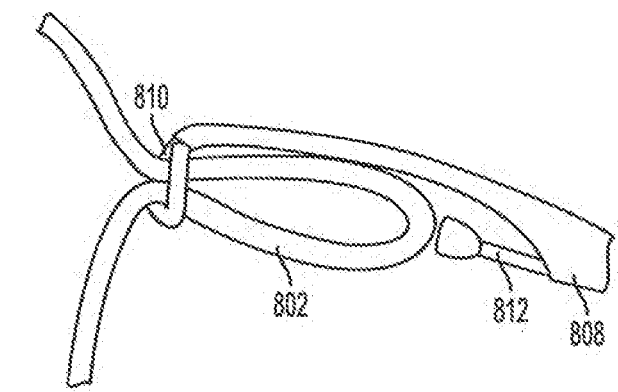

When a balloon catheter or guide element comprises a balloon and one or more electrodes and/or abrading elements proximally to the balloon, the electrodes and/or abrading elements may ablate and/or abrade, respectively, interior tissue of the left atrial appendage. For example, FIGS. 8A and 8B depict such an illustrative closure method. As shown in FIG. 8A, a balloon (800) may be advanced into the left atrial appendage (802). In some variations, the balloon (800) may be part of a balloon catheter (804) (such as the balloon catheter (700) described above with respect to FIG. 7A or the balloon catheter (710) described above with respect to FIG. 7B), and the balloon catheter (804) may be advanced along a first guide element (806), such as described above. In other variations, the balloon (800) may be part of the first guide element (such as the guide element (720) shown in FIG. 7C or the guide element (730) shown in FIG. 7D), such that advancement of the first guide element (806) into the left atrial appendage (802) also positions the balloon (800) in the left atrial appendage.

A closure device (808) may be advanced externally of the heart to position a closure assembly (810) of the closure device (808) around external tissue of the left atrial appendage (802). The closure device (808) may be advanced in any suitable manner, such as, for example, along a second guide element (812) that is positioned in the pericardial space, such as discussed in more detail above (the first and second guide elements may include magnets that may align the first and second guide elements across tissue of the left atrial appendage). Generally, the closure device (808) may be advanced to position the closure assembly past the balloon (800) (e.g., such that the closure device (808) is positioned around a portion of the balloon catheter (804) and/or first guide element (806) proximal to the balloon (800)), such as shown in FIG. 8A. As mentioned above, the balloon catheter (804) (or first guide element (806) in variations where the balloon (800) is part of the first guide element (806)) may comprise one or more elements (814), which may include one or more electrodes and/or abrading elements, such as discussed above.

With the closure device (808) and balloon (800) positioned as shown in FIG. 8A, the closure assembly (810) may be closed to place the left atrial appendage into contact with one or more of the elements (814). In variations where the one or more elements (814) comprise an electrode, the electrode may be activated to ablate the interior left atrial appendage tissue in contact with the electrodes. In variations where the one or more elements (814) comprise an abrading element, the abrading element may be moved relative to the interior left atrial appendage tissue to abrade that issue. In some variations, this may comprise rotating and/or longitudinally translating the balloon catheter (804) (or the first guide element (806) in variations where the abrading element is part of the first guide element (806)) to move the abrading element relative to the tissue to abrade the interior tissue of the left atrial appendage. In other variations, the abrading element may be moveable relative to the balloon catheter (804) and/or the first guide element (806), and may be actuated to move the abrading element relative to tissue to abrade the tissue.

Once the tissue has been abraded and/or ablated, the balloon (800), the balloon catheter (804) (in variations where the balloon (800) is part of the balloon catheter (804), and the first guide element (806) may be removed, and the closure assembly (810) may be further closed to close the left atrial appendage (802), as shown in FIG. 8B.

Figure 9A:
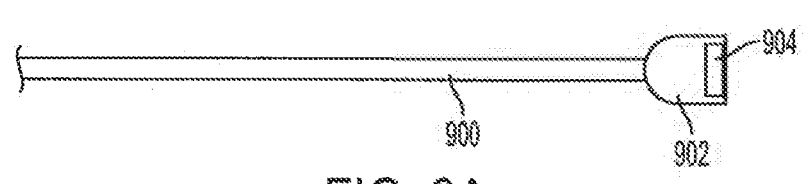
FIGS. 9A and 9B depict side views of illustrative variations of guide elements suitable for use with the systems described here.

In some variations, the distal end of a guide element may be configured to ablate interior tissue of the left atrial appendage. For example, FIG. 9A shows a variation of a guide element (900) as described here. As shown in FIG. 9A, the guide element may comprise a magnet (902) positioned at a distal end of the guide element (900). Also shown there is an electrode (904) positioned at a distal end of the guide element (900). The electrode may be used to ablate interior tissue of the left atrial appendage, as will be described in more detail below. In some embodiments, the guide element may be configured to deliver or dispense fluid to surrounding tissue.

Figure 9B:
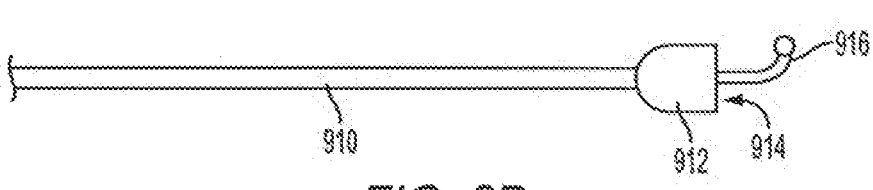

In other variations, a wire or other member may be advanced from a distal end of the guide element, and may be configured to act as an electrode to ablate tissue. For example, FIG. 9B shows another variation of a guide element (910) as described here. As shown there, the guide element (910) may comprise a magnet (912) at a distal end of the guide element (910), and may comprise a lumen (914) extending through the guide element (910). The guide element (910) may further comprise a wire (916) which may be advanced through the lumen (914) to extend from a distal end of the guide element (910). A proximal end of the wire (916) may be connected to an energy source (not shown) such that the wire (916) may act as an electrode to ablate tissue. In some variations, a proximal end of the wire (916) may be connected to a source of cryogenic fluid such that the wire (916) may be used to cryoablate tissue. In some embodiments, the wire (916) may comprise a lumen such that it may be used to dispense fluid to the surrounding tissue. The fluid may be delivered through the lumen and either out of the distal tip of the wire (916) or through side apertures along the wire's distal end. The proximal end of the wire (916) may be connected to a source of fluid, for example, a therapeutic compound or an adhesive, and the wire (916) may be used to deliver and dispense the fluid to locally affect (e.g., promote healing or closure) the surrounding tissue. The wire (916) may be any suitable wire. For example, the wire (916) may be a straight-tip or j-tip wire, may be a coiled wire, or may be configured to make another 3-dimensional shape. In some of these variations, the wire may be a ball-tipped wire.

Figures 10A, 10B, 10C:
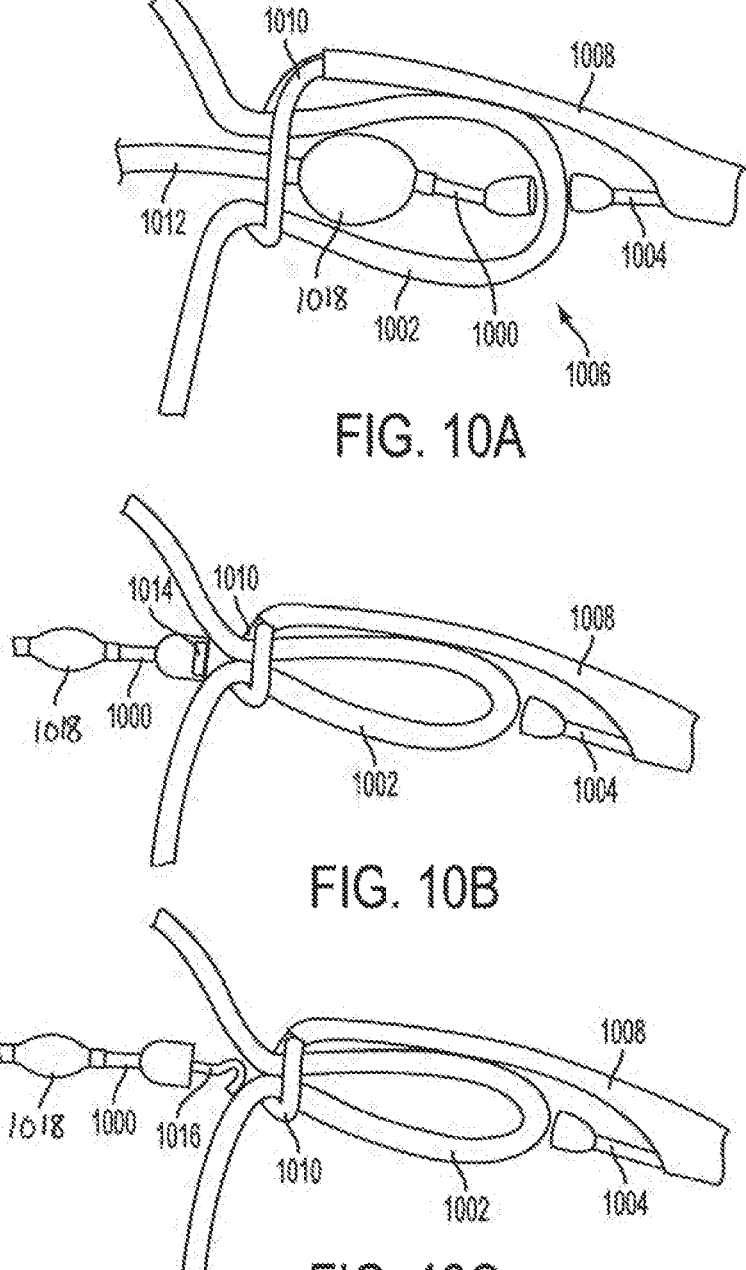
FIGS. 10A-10C depict variations of methods as described here.

When a guide element has an electrode or electrode wire at its distal end (such as the guide elements (900) and (910) described above with respect to FIGS. 9A and 9B, respectively), the guide element may be used to ablate interior tissue of the left atrial appendage. For example, FIGS. 10A-10C shows two such variations of a method of closing a left atrial appendage. As shown in FIG. 10A, a first guide element (1000) may be positioned inside the left atrial appendage (1002) and a second guide element (1004) may be positioned externally of the left atrial appendage (1002) in the pericardial space (1006). In some variations, the first guide element (1000) and the second guide element (1004) may be aligned using magnets on each of the guide elements, such as discussed in more detail above. A closure device (1008) may be advanced over the second guide element (1004) to position a closure assembly (1010) around exterior tissue of the left atrial appendage (1002). In some variations, a balloon (1018) may be positioned in the left atrial appendage (1002) (either as part of a balloon catheter (1012) or the first guide element (1000)), such as discussed in more detail below.

With the closure assembly (1010) of the closure device (1008) encircling the left atrial appendage (1002), the first guide element (1000) (and the balloon catheter (1012) in variations where a balloon catheter (1012) is at least partially advanced into the left atrial appendage (1002)) may be removed from the interior of the left atrial appendage (1002) and the closure assembly (1010) may be closed to close the left atrial appendage (1002). After the left atrial appendage (1002) is closed, the first guide element (1000) may be re-advanced to ablate, join or bond, or deliver drugs to the closed left atrial appendage tissue.

For example, in variations where the first guide element (1000) comprises an electrode (1014) at a distal end of the first guide element (1000), the first guide element (1000) may be re-advanced to place the electrode (1014) into contact with the interior tissue of the left atrial appendage (1002), as shown in FIG. 10B. Generally, this may place the electrode (1014) into contact with tissue around the ostium of the left atrial appendage (1000). The electrode (1014) may deliver RF energy to the tissue of the left atrial appendage (1002) to ablate the tissue. In some variations, the first guide element (1000) may be used with cryogenic fluid to cryoablate tissue. In some embodiments, the closure device (1008) may comprise a magnetic tip (e.g., tip (110) depicted in FIG. 1) or a magnet on its distal end to assist in guiding the distal end of the first guide element (1000) into contact with the interior tissue of the left atrial appendage (1002) in embodiments in which the first guide element (1000) comprises a magnet, as described above.

In variations where the first guide element (1000) is configured to advance a wire (1016) out of a distal end of the first guide element (1000), the wire (1016) may be advanced from a distal end of the first guide element (1000) to expose a portion of the wire (1016), and the wire (1016) may be positioned in contact with the tissue around the ostium of the left atrial appendage (1002), such as shown in FIG. 10C. In some instances this may comprise advancing the first guide element (1000) and the wire (1016) together. With the wire (1016) in contact with left atrial appendage tissue, the wire (1016) may be activated as an electrode to ablate the tissue, may be used with cryogenic fluid to cryoablate the tissue, or may be configured to locally deliver fluid, as described above.

It should be appreciated that the methods described above with respect to FIGS. 10A-10C may be used with any of the methods described above with respect to FIGS. 6A-6C and 8A-8B. In these variations, interior tissue of the left atrial appendage may be ablated or abraded, and may be closed to press the ablated/abraded tissue into contact with itself (which may assist in electrical isolation and/or invoking a healing response). The closed ostium of the left atrial appendage may then be ablated or abraded to further promote electrical isolation of the left atrial appendage and/or a healing response.

Figures 11A, 11B, 11C:
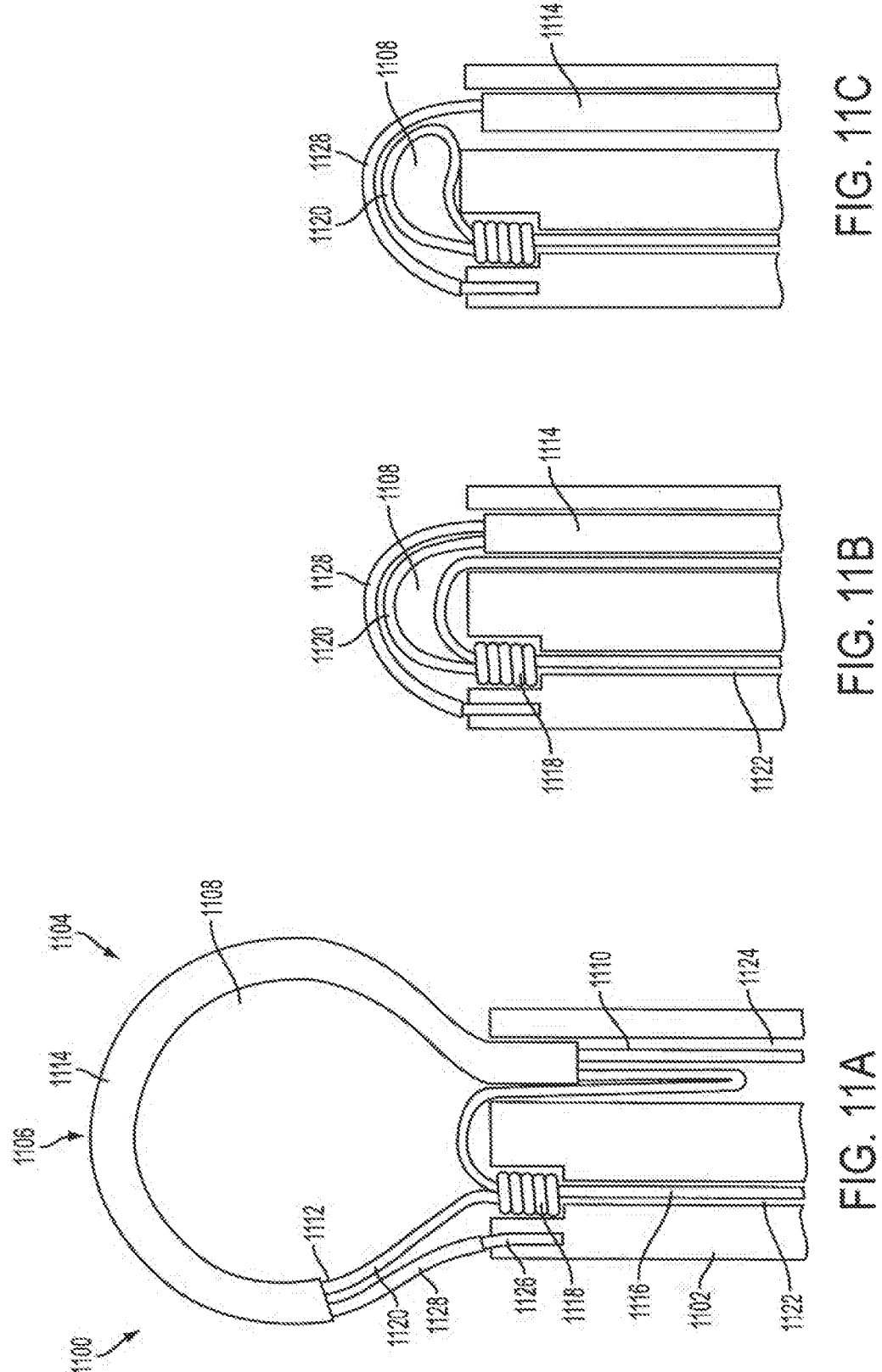
FIGS. 11A-11C, 12A-12C, and 13A-13C depict cross-sectional side views of three variations of closure devices as described here.

In addition to or as an alternative to ablating or abrading the interior tissue of the left atrial appendage, the closure devices described here may be configured to ablate exterior tissue of the left atrial appendage. FIGS. 11A-11C show cross-sectional side views of a distal portion of one such variation of a closure device (1100). As shown there, the closure device (1100) may comprise an elongate body (1102) and a snare loop assembly (1104), which may define a loop (1106) encircling an aperture (1108). The snare loop assembly (1104) may comprise a snare (1110), a suture loop (1112), and retention member (1114), such as discussed in more detail above. The suture loop (1112) may include a tail portion (1116), a suture knot (1118), and a loop portion (1120), such that one end of the snare (1110) extends through a first lumen (1124) in the elongate body (1102) and the tail portion (1116) of the suture loop (1112) extends through a second lumen (1122) in the elongate body. A second end (1126) of the snare (1110) may be fixed relative to the elongate body (1102). As discussed in more detail above, movement of the snare (1110) into and out of the first lumen (1124) may increase and decrease the size of the loop (1106) defined by the snare loop assembly (1104).

Also shown in FIGS. 11A-11C is an electrode (1128). The electrode (1128) may be positioned around a portion of the snare loop assembly (1006). In the variation shown in FIGS. 11A-11C, the electrode (1128) may be positioned on the snare (1110) between the fixed end (1126) of the snare (1110) and the retention member (1114), but not around the suture loop (1112). In some variations, a portion of the snare (1110) may act as an electrode (1128). Specifically, the snare (1110) may be formed from an electrically conductive material which may convey current from a proximal portion of the snare to the electrode (1128). The snare (1110) may be at least partially covered with an insulating material (such as PTFE), such that the insulating material insulates portions of the snare (1110) to prevent inadvertent ablation by the snare. The electrode (1128) may not include the insulating material to expose the conductive material of the snare (1110), which may thereby act as an electrode. It should be appreciated that the snare may also be used with cryogenic fluid (e.g., within a lumen of the snare) such that the snare may cryoablate the tissue. The snare may also comprise porous materials or apertures such that the snare may be used to dispense therapeutic compounds, adhesive, or any other desired material to the tissue. Moreover, in some variations, the electrode (1128) may comprise magnetic material or may be an electromagnet. In these variations, when the snare (1110) is closed around the external surface of the left atrial appendage, the magnetic material of electrode (1128) may externally encircle the left atrial appendage which may assist in guiding a tool (e.g., an ablation or abrading device) within the left atrial appendage or the left atrium to the closure site.

Figures 12A, 12B, 12C:
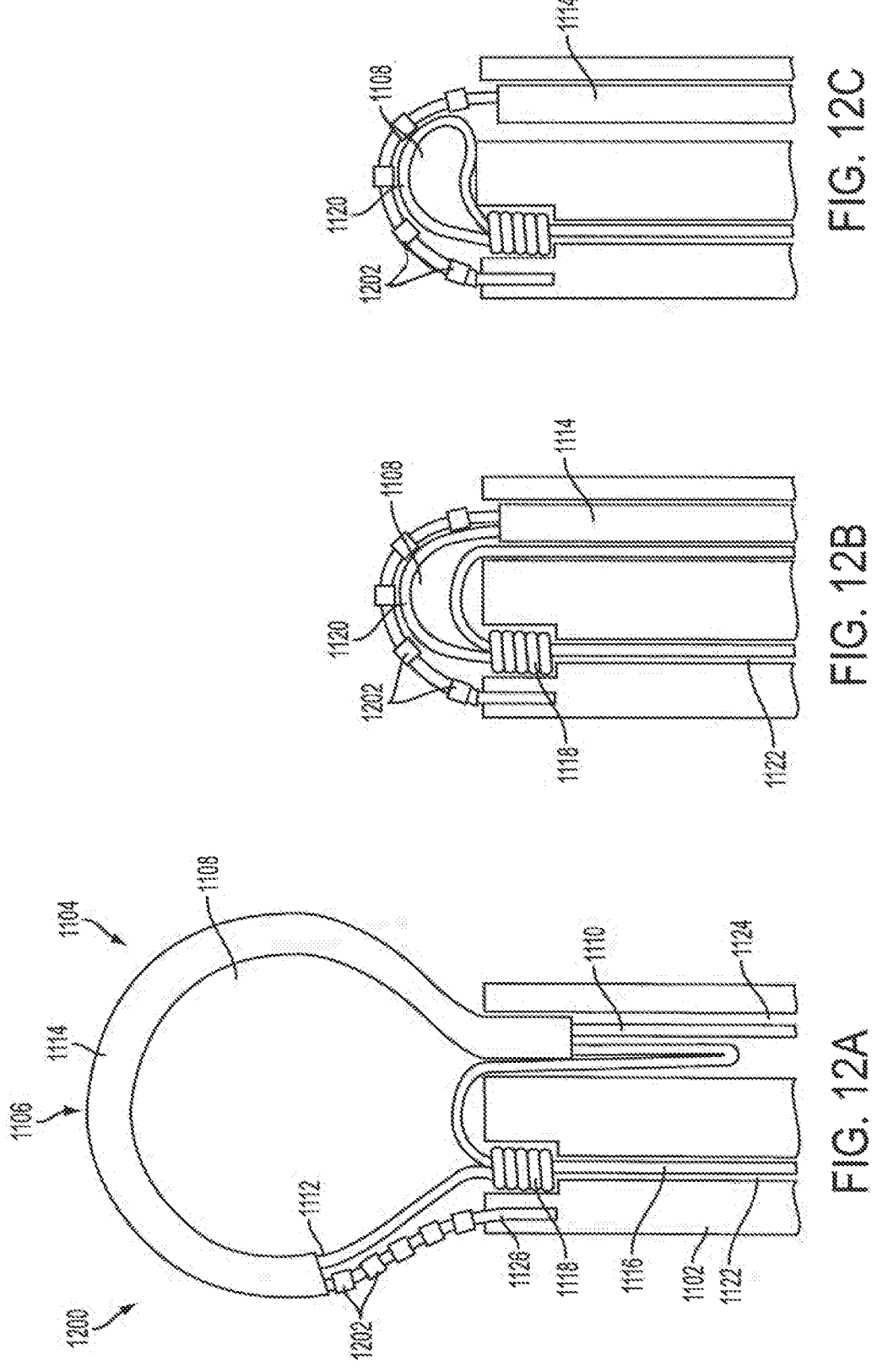

While shown in FIGS. 11A-11C as having a single electrode (1128), the closure device 1100) may comprise any suitable number of electrodes (e.g., one, two, three, or four or more electrodes). For example, FIGS. 12A-12C show another variation of a closure device (1200) having a plurality of electrodes (1202). The closure device (1200) may comprise a snare loop assembly (1104) and an elongate body (1102) as discussed above with respect to FIGS. 11A-11C (identical components are labeled as shown in FIGS. 11A-11C). As shown in FIGS. 12A-12C, the closure device may include a plurality of electrodes (1202) positioned on the snare (1110) between the fixed end (1126) of the snare (1110) and the retention member (1114). While shown in FIGS. 12A-12C as having five electrodes (1202), the snare (1110) may include any suitable number of electrodes as discussed above. In variations where the snare (1110) includes multiple electrodes (1202), some electrodes may be used to ablate tissue, while other electrodes may be used to monitor one or more aspects of tissue (e.g., one or more electrical signals, temperature, or the like).

Additionally, as described above with respect to electrode (1128), electrodes (1202) may comprise magnetic material or electromagnets. Moreover, in some variations, one or more of the elements (1202) may be replaced by magnets. In variations in which the elements (1202) comprise both electrodes and magnets, the electrodes and magnets may be arranged along the snare in any suitable configuration, for example, alternating every other element, in pairs, in groups, etc. The magnets may assist a user in locating the desired area inside of the heart as the magnets on the snare may help align a tool inside of the heart with the closure location. Additionally, in embodiments in which the elements (1202) comprise both magnets and electrodes, a user may ablate an external surface of the left atrial appendage with the electrodes and utilize the magnets to align an internal tool (ablating, abrading, or other tissue affecting device) with the external electrodes to ablate or otherwise affect the tissue at substantially the same location.

The closure devices (1100) and (1200) shown in FIGS. 11A-11C and 12A-12C respectively, may be used to ablate tissue of the left atrial appendage. For example, the snare loop assembly (1104) may be placed in an open configuration, as shown in FIGS. 11A and 12A, and may be advanced into the pericardial space to position the left atrial appendage (not shown) in the aperture (1108) of the snare loop assembly. The snare loop assembly (1104) may be closed around the left atrial appendage to close the left atrial appendage, as shown in FIGS. 11B and 12B. This may position the electrode (1128) (in the instance of the closure device (1100)) or one or more of the electrodes (1202) (in the instance of the closure device (1200)) in contact with exterior tissue of the left atrial appendage. In some instances, the exterior tissue of the left atrial appendage may be ablated at this point.

In some variations, the suture loop (1112) may be tightened to release the suture loop from the retention member (1114) and the snare loop assembly (1104), such as shown in FIGS. 11C and 12C. In some variations, the exterior tissue of the left atrial appendage may be ablated using the electrode (1128) or one or more of the electrodes (1202) after the suture loop (1112) has been released from the snare loop assembly (1104). This may be done in addition to or instead of ablation prior to the release of the suture loop (1112). In some variations, the snare loop assembly (1104) may be reclosed around the left atrial appendage prior to ablation to tighten the snare loop assembly (1104) against tissue. In some variations, the snare loop assembly (1104)

may be reopened, repositioned, and reclosed around the left atrial appendage prior to ablation.

Figures 13A, 13B, 13C:
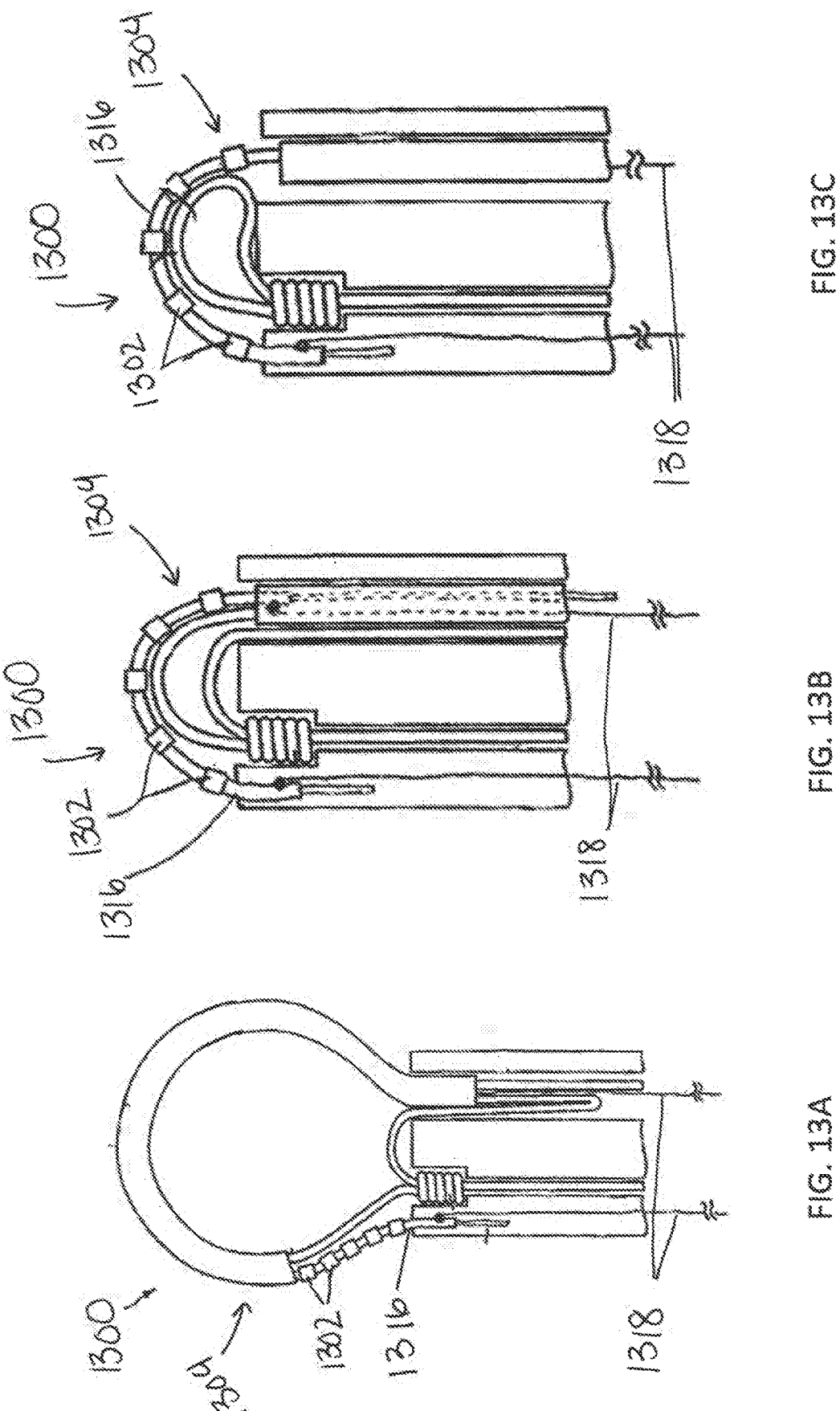

The closure device (1300) depicted in FIGS. 13A-13C may be used to abrade tissue of the left atrial appendage. As shown there, the closure device (1300) comprises a snare loop assembly (1304) similar to that described with respect to FIGS. 11A-11C and 12A-12C above, except that the snare loop assembly (1304) comprises a plurality of abrading elements (1302) instead of, or in addition to, a plurality of electrodes. The abrading elements (1302) may be disposed on an abrading member (1316) (e.g., tubing) that is slideably disposed on the snare. The abrading member (1316) may be coupled to an actuator (not depicted) on the handle or control element of the closure device (1300) through control wires (1318). A user may actuate the abrading member (1316) by alternatingly pulling the control wires (1318) such that the abrading member (1316) slides along the snare (1310). The abrading elements (1302) fixed to the abrading member (1316) are thus moved in a reciprocating motion and may be used to abrade tissue. It should be appreciated that the abrading elements (1302) may also comprise one or more electrodes to ablate tissue.

We claim:

1. A method of closing an atrial appendage comprising:
positioning a balloon at least partially within an interior of the atrial appendage;
positioning a closure assembly of a closure device around an exterior of the atrial appendage, wherein the closure assembly comprises a loop;
inflating the balloon at least partially within the interior of the atrial appendage;
partially closing the loop to close the atrial appendage around the inflated balloon;
ablating the interior tissue of the atrial appendage with the inflated balloon;
removing the balloon from the atrial appendage through the closure assembly; and
closing the atrial appendage with the closure assembly.

2. The method of claim 1, further comprising positioning a distal end of a first guide element in the interior of the atrial appendage and positioning a distal end of a second guide element in a pericardial space externally of the atrial appendage.

3. The method of claim 2, wherein the first guide element and the second guide element each comprise a magnet, and further comprising aligning the first guide element and the second guide element across tissue of the atrial appendage.

4. The method of claim 2, wherein positioning a closure device comprises advancing the closure device along the second guide element.

5. The method of claim 2, wherein the balloon is part of the first guide element.

6. The method of claim 2, wherein the balloon is part of a balloon catheter and wherein positioning the balloon comprises advancing the balloon catheter along the first guide element.

7. The method of claim 1, wherein the balloon comprises an electrode positioned on an exterior surface of the balloon, and wherein ablating the interior tissue of the atrial appendage comprises ablating the interior tissue of the atrial appendage with the electrode.

8. The method of claim 7, wherein the balloon comprises at least two electrodes, the method further comprising monitoring a tissue parameter with at least one of the electrodes during ablation of the interior tissue.

9. The method of claim 1, wherein ablating the interior tissue of the atrial appendage comprises cryoablating the interior tissue of the atrial appendage.

10. The method of claim 1, wherein ablating the interior tissue of the atrial appendage comprises ablating the interior tissue of the atrial appendage using heated fluid contained in the balloon.

11. The method of claim 1, further comprising releasing the loop from the closure assembly to hold the atrial appendage closed.

12. The method of claim 1, wherein the closure assembly comprises an electrode, and further comprising ablating an exterior of the atrial appendage with the electrode.

13. The method of claim 1, further comprising cryoablating an exterior surface of the atrial appendage with the closure assembly.

14. A method of closing an atrial appendage comprising:
positioning a distal end of a first guide element in the interior of the atrial appendage;
advancing a balloon catheter along the first guide element, wherein the balloon catheter comprises a balloon;
positioning a distal end of a second guide element in a pericardial space externally of the atrial appendage, wherein the first guide element is aligned across the second guide element on opposite sides of the heart;
advancing a closure assembly of a closure device around an exterior of the atrial appendage along the second guide;
inflating the balloon within the atrial appendage;
withdrawing the first guide element from the interior of the atrial appendage; closing the atrial appendage with the closure assembly;
advancing a portion of the first guide element into contact with tissue around an ostium of the closed atrial appendage; and
ablating the contacted tissue with the first guide member.

15. The method of claim 14, wherein the first guide element and the second guide element each comprise a magnet, and further comprising aligning the first guide element and the second guide element across tissue of the atrial appendage.

16. The method of claim 14, wherein the first guide element comprises an electrode positioned at the distal end of the first guide element.

17. The method of claim 14, further comprising advancing a wire from a distal end of the first guide element, wherein advancing a portion of the first guide member into contact with tissue around the ostium of the closed atrial appendage comprises advancing the wire into contact with the tissue around the ostium of the closed atrial appendage.

18. The method of claim 17, further comprising cryoablating the tissue around the ostium with the wire.

19. The method of claim 14, wherein the closure assembly comprises an electrode, the method further comprising ablating an exterior of the atrial appendage with the electrode.

20. The method of claim 14, further comprising cryoablating an exterior surface of the atrial appendage with the closure assembly.

* * * * *